(12) United States Patent
Lee et al.

(10) Patent No.: US 6,793,802 B2
(45) Date of Patent: Sep. 21, 2004

(54) BIOSENSORS HAVING IMPROVED SAMPLE APPLICATION AND MEASURING PROPERTIES AND USES THEREOF

(75) Inventors: Jin Po Lee, Carlsbad, CA (US); Tong-Yuh Huang, Taitung (TW)

(73) Assignee: Tyson Bioresearch, Inc., Taiwan (CN)

( * ) Notice: Subject to any disclaimer, the term of this patent is extended or adjusted under 35 U.S.C. 154(b) by 358 days.

(21) Appl. No.: 09/754,858

(22) Filed: Jan. 4, 2001

(65) Prior Publication Data

US 2004/0031698 A1 Feb. 19, 2004

(51) Int. Cl.[7] .......................................... G01N 27/327
(52) U.S. Cl. .............................. 205/777.5; 204/403.14; 204/401
(58) Field of Search ................. 204/403.01, 403.04, 204/403.14, 416, 401; 205/777.5

(56) References Cited

U.S. PATENT DOCUMENTS

| | | | |
|---|---|---|---|
| 4,999,582 A | 3/1991 | Parks et al. | 324/438 |
| 5,120,420 A | 6/1992 | Nankai et al. | 204/403 |
| 5,264,103 A | * 11/1993 | Yoshioka et al. | 205/778 |
| 5,288,636 A | 2/1994 | Pollmann et al. | 435/288 |
| 5,320,732 A | 6/1994 | Nankai et al. | 204/403 |
| 5,508,171 A | 4/1996 | Walling et al. | 205/777.5 |
| 5,628,890 A | 5/1997 | Carter et al. | 204/403 |
| 5,708,247 A | 1/1998 | McAleer et al. | 204/403 |
| 5,762,770 A | 6/1998 | Pritchard et al. | 204/403 |
| 5,997,817 A | 12/1999 | Crismore et al. | 204/403.1 |

FOREIGN PATENT DOCUMENTS

| | | | |
|---|---|---|---|
| EP | 0735363 | 10/1996 | G01N/27/327 |
| EP | 0851224 | 7/1998 | G01N/27/327 |
| EP | 0909952 | 4/1999 | G01N/33/487 |
| JP | 02-310457 | * 12/1990 | G01N/27/327 |
| JP | 402310457 | 12/1990 | G01N/27/327 |

OTHER PUBLICATIONS

JPO abstract of Kawaguri et al. (JP 02–310457 A) Dec. 1990.*
Anzai et al., Anal. Chem. (1998) 70(4):811–817 Feb. 15.
Kureishi et al., Bioelectrochem. Bioenerg. (1999) 48(1):95–100.
Stonehuerner et al., Biosens. Bioelectron. (1992) 7(6):421–428.
International Preliminary Examination Report, mailed on Nov. 6, 2003, for PCT patent application No. PCT/US01/11133, filed on Apr. 6, 2001, 7 pages.

* cited by examiner

Primary Examiner—Alex Noguerola
(74) Attorney, Agent, or Firm—Morrison & Foerster LLP

(57) ABSTRACT

The present invention relates to biosensors having improved sample application and measuring properties and their uses for detection, preferably, quantitative measurement, of analyte in a liquid sample. In particular, the invention provides for a biosensor having a sample application and reaction chamber facilitating the speed and uniformity of sample application, especially small volume sample application, via capillary flow. The invention also provides for a biosensor having multiple circuits that lead to improved assay consistency and accuracy. Methods for assaying analytes or enzymes using the biosensors are further provided.

49 Claims, 10 Drawing Sheets

Layer 1: The Insulating Layer
Layer 2: The Electrode Layer
Layer 3: The Dielectrical Layer
Layer 4: The Covering Lamina

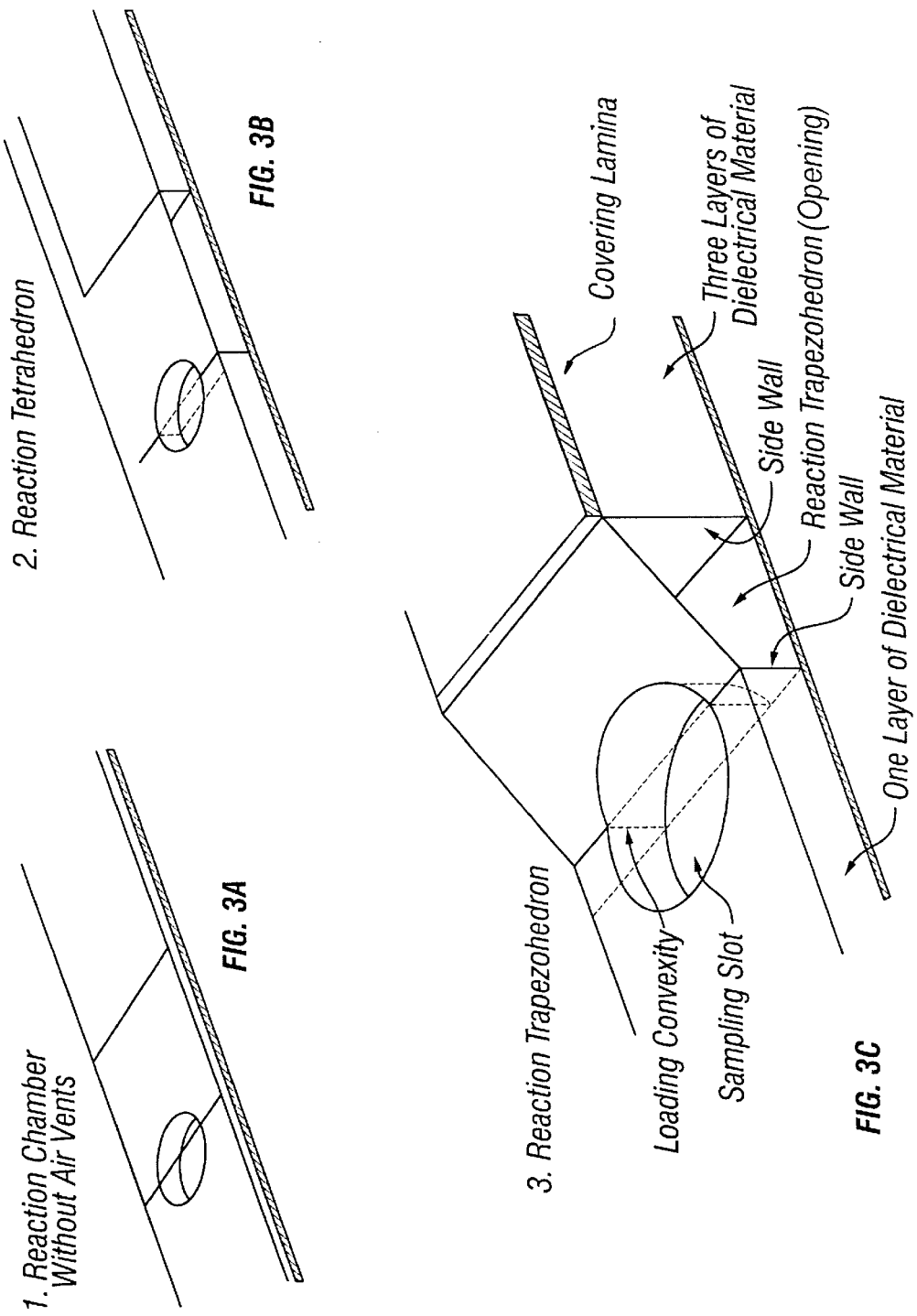

1. Sample Introduction from the Top Side

2. Sample Introduction from the Bottom Side

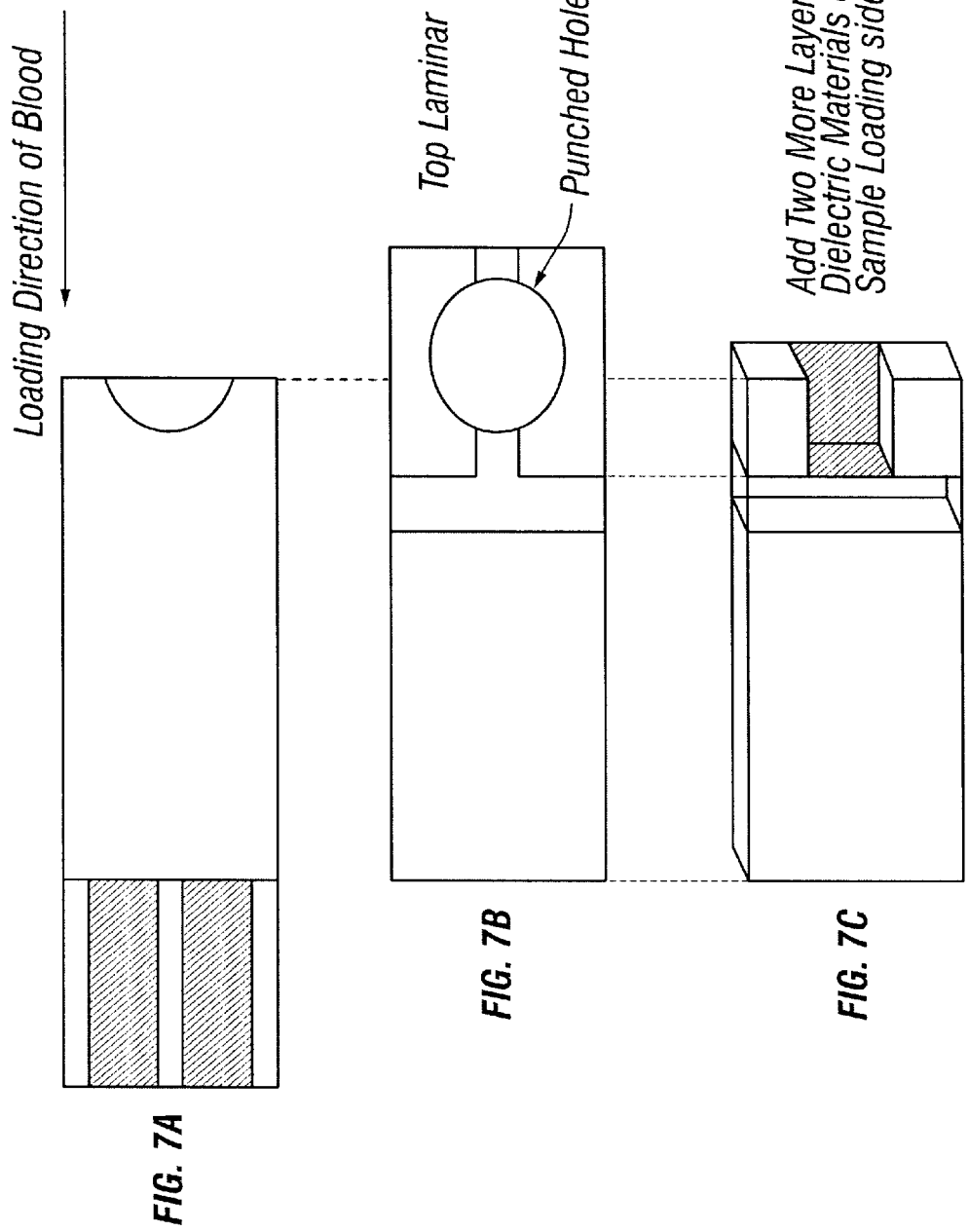

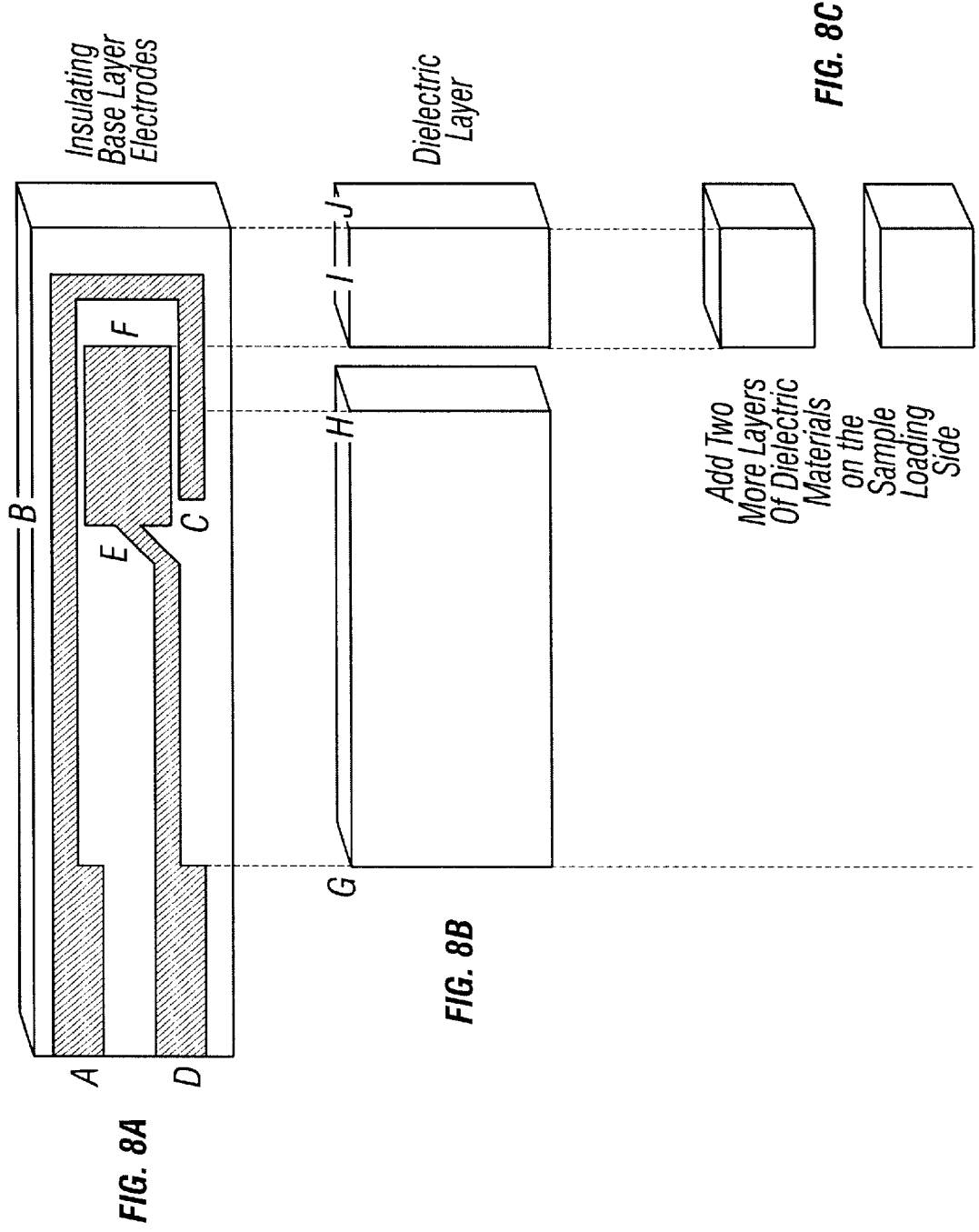

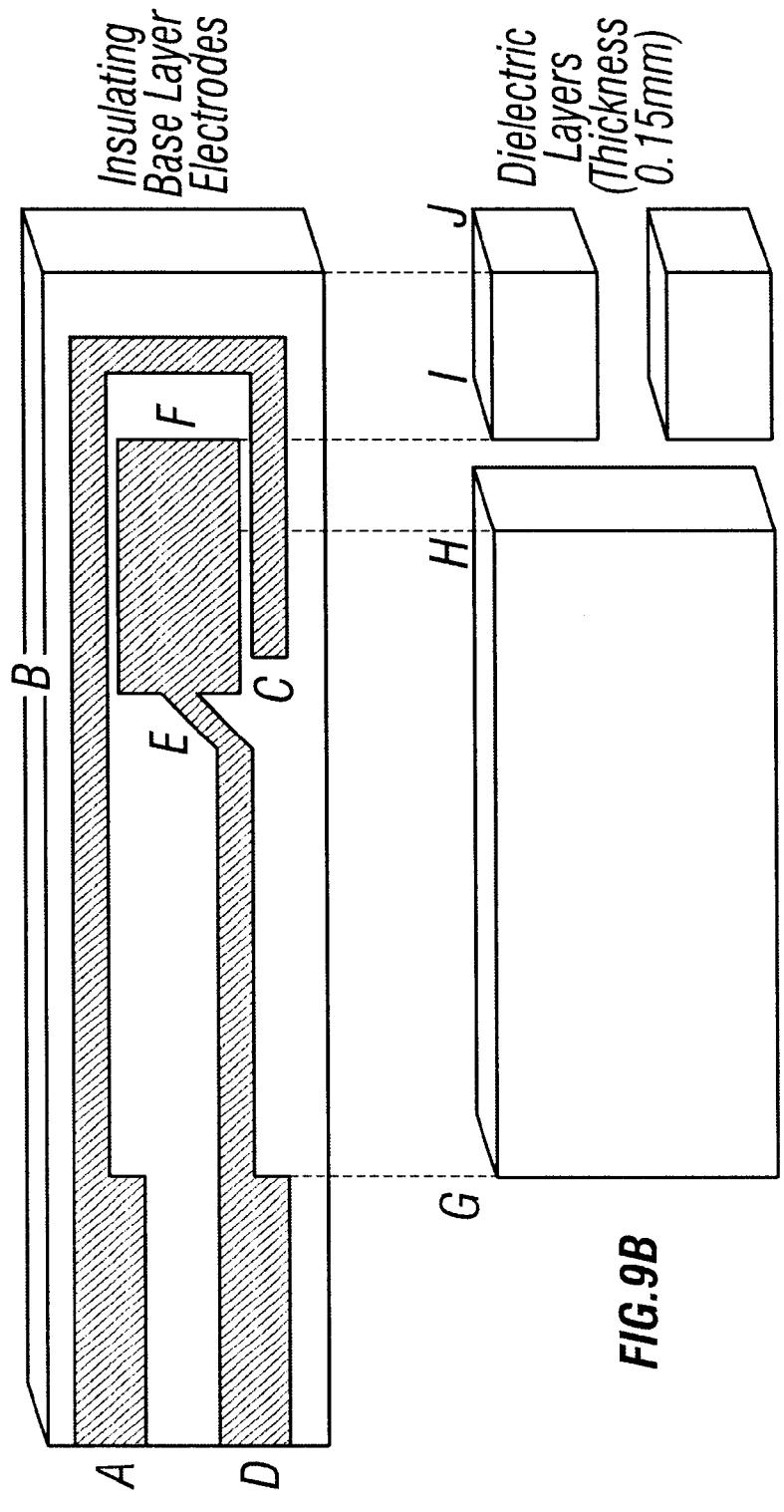

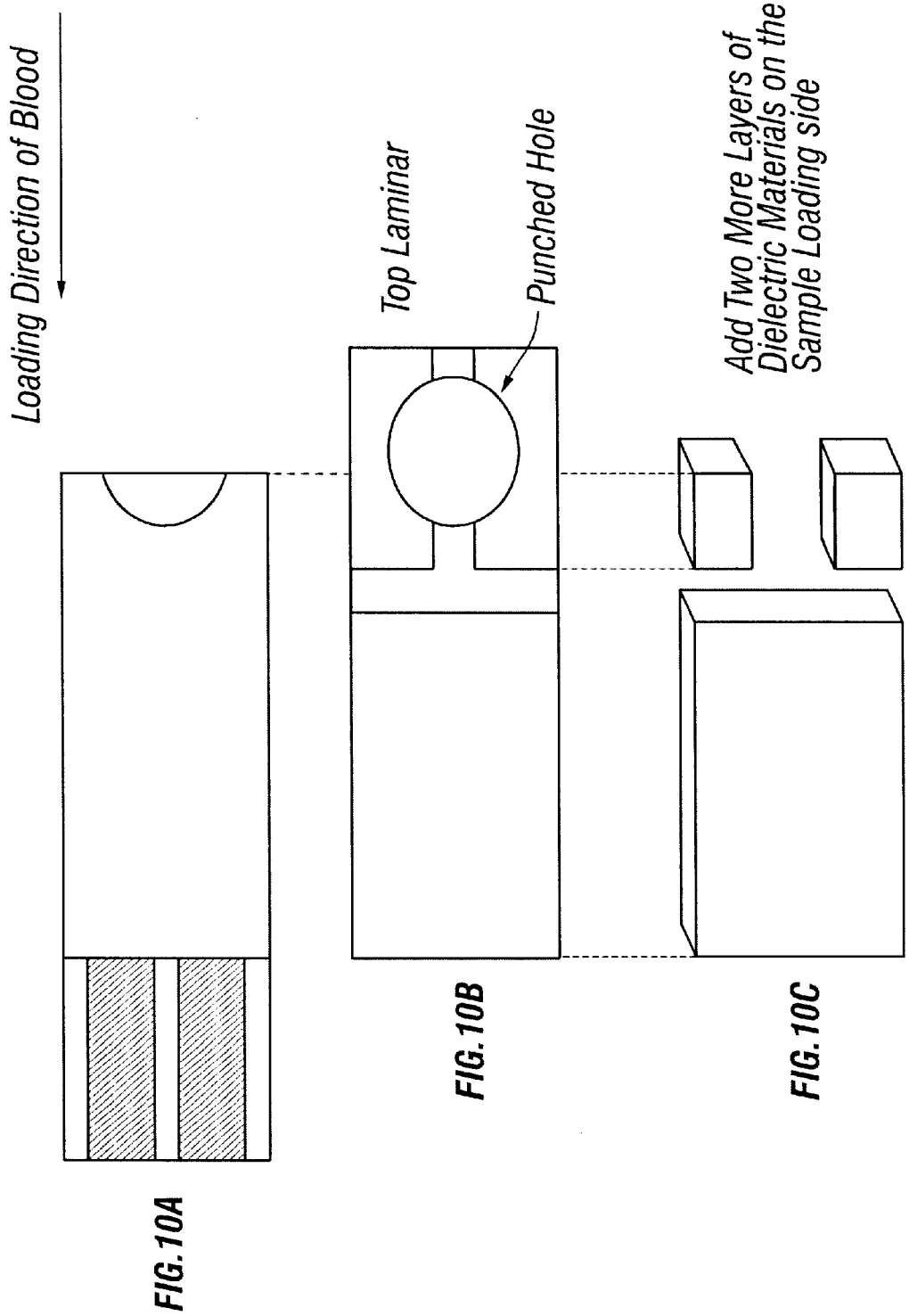

BIOSENSORS HAVING IMPROVED SAMPLE APPLICATION AND MEASURING PROPERTIES AND USES THEREOF

FIELD OF THE INVENTION

The present invention relates to biosensors having improved sample application and measuring properties and their uses for detection, preferably, quantitative measurement, of analyte or enzyme in a liquid sample. In particular, the invention provides for a biosensor having a sample application and reaction chamber facilitating the speed and uniformity of sample application, especially small volume sample application, via capillary flow. The invention also provides for a biosensor having multiple circuits that lead to improved assay consistency and accuracy. Methods for assaying analytes or enzymes using the biosensors are further provided.

BACKGROUND OF THE INVENTION

A biosensor is an analytical device that comprises at least two components: an immobilized biological component responsible for the selective recognition of the test species and a suitable transducer device responsible for relaying the biological signals for further analysis. Among others, electrochemical biosensors that employ biological recognition systems and electrochemical transudation offer a possibility of quick and real-time analysis, which is particularly suited for the rapid measurement of point-of-care industry. The evolution of these devices comes from the multi-discipline of electronics, material science, electrochemistry, biochemistry, and immunochemistry. The technology of electroanalysis is an interplay between electricity and chemistry that concerns current, potential, and charge from a chemical reaction. There are two principal types of electroanalytical measurements, potentiometric and amperometric. Potentiometric technique is a static technique with no current flow; the established potential across the ion-select membrane is measured. With different types of membrane materials, the recognition of different ions can be reached. Thus, the potentiometric probes have been widely used for directly monitoring ionic species such as calcium, potassium, and fluoride ions. In amperometric technique, an electrode potential is used to drive an electron-transfer reaction. The responsive current is measured and related to the presence and/or concentration of the target analyte. In the past, potentiometric devices have been more widely applied in clinical chemistry laboratories. But with increasing amount of research on amperometric systems in diagnostics, the balance has shifted. The amperometric biosensors make possible a practical, fast, and routine measurement of test analysts. The trend of new generations of biosensors focuses on the methodology of minimum demand of operator skills and least sample pretreatment.

Up to date, most commercially used biosensors are amperometric ones that harness redox enzymes as recognizing biocomponents and electrodes as electrochemical transducers. The mass production of inexpensive and disposable devices has been achieved recently with the help of screen-printing technology. The success in the development of these devices has led to amperometric assays for several biomolecules including glucose, cholesterol, and various drugs. This type of amperometric biosensor is typically composed of an insulating base plate, two or three electrodes, a dielectric layer, and a region for enzymatic reaction. Two-electrode biosensor consists of a working electrode, a counter electrode and a destined region where reagent for enzymatic reaction is placed. The reaction progresses when the sample liquid containing an analyte is applied onto the reaction area. Two physical effects, mesh spread and capillary action, are commonly used to guide a uniform distribution of the loaded sample on the reaction area. After the reaction is complete, the test analyte is oxidized and the electrons yielded from the reaction are trapped in a reduced co-product. A controlled-potential is then applied between the electrodes to trigger a second round of oxidoreduction. This electrical potential must be sufficient enough to drive a diffusion-limited electrooxidation at the surface of the working electrode, yet insufficient to activate irrelevant chemical reactions. After a short time of delay, the current produced by the electrochemical oxidoreduction is observed and measured and the current is correlated to the presence and/or amount of the analyte in the sample.

In the case of oxidation, oxygen is consumed in the oxidative reaction as a co-reactant and hydrogen peroxide is yielded as a co-product. Th peroxide is proportional to the concentration of analyte. Hydrogen peroxide can be detected by oxidizing it at anodic potential (e.g., >0.6 V, Ag/AgCl) to generate an electrical signal (current). However, the potential required for oxidizing hydrogen peroxide can cause oxidation of other oxidizable chemicals such as ascorbate, bilirubin, uric acid, and the commonly used drug, e.g., acetaminophen, thus leading to an interference of electrical current to be detected. This interference can be avoided by replacing oxygen with an artificial mediator capable of transferring electrons from oxidoreductases. Several mediators have been used to enhance electron transfer between a variety of enzymes and electrodes, which include ferrocene and its derivatives, osmium complex, tetrathiofulvalene, phenazine ethosulfate, benzoquinone, and hexacyanoferrate.

In the conventional way of determining analytes in blood, a pretreatment of samples is required. A direct measurement of whole blood samples is in need of providing a simple way to save time and labor. More importantly, direct measurement of whole blood samples makes it possible for a real time monitoring for home users. For accurate measurement of a whole blood sample using an amperometric biosensor, a quick and homogenous reaction on the electrodes is essential for a successful analyte determination. The dried reagents including an oxidoreductase and a mediator have to dissolve instantly when a small volume of sample blood is applied to the biosensor. These dissolved reagents have to mix with sample blood thoroughly for the completion of the enzymatic reaction and the consistency of the subsequent electronic reaction.

The other common problems for assaying biological samples such as the whole blood are sample viscosity and the relatively large sample volume for the analysis. The whole blood sample, with its viscosity, might not be able to be distributed over sufficient reaction area. For some poorly breeding people, it might be a problem to get enough blood from a prick on fingerstick. Three types of insufficient application of blood (or other viscous samples) have been observed: first, the sample covers only the front end of the test strip; secondly, the sample covers only the right half of the strip; and thirdly, the sample covers only the left half of the strip. The insufficient or non-homogenous application of sample fluid presents a lower amount of analyte, which causes an artificial and misleading lower result.

Accordingly, there is a need in the art for biosensors and methods that provide for improved sample application and measuring properties. The present invention addresses this other related needs in the art.

BRIEF DESCRIPTION OF THE INVENTION

In one aspect, the present invention provides for a biosensor with which the sample fluid is distributed into destined reaction area rapidly, uniformly and economically. It is another object of this invention to provide a sampling slot with least contact with reagent. Sample fluid, e.g., blood, can be loaded by a punched hole on this sampling slot and can be drawn to the reaction area quickly facilitated by an outward surface tension provided by the arcuate portion of the sampling slot and a pull-up action provided by the reaction chamber. A homogenous distribution of sample fluid can be achieved and the analyte works as a substrate to trigger the enzymatic reaction and starts the test. It is still another aspect of this invention to provide for a special design of the electrodes in a way that an elevation of electronic flow is made possible by increasing the diffusion surface between the working electrode and counter electrode. This way, the diffusion of electroactive chemicals is also uniform since both electrodes are of equal reaction areas and of the same material.

In a specific embodiment, a biosensor for electrochemical analysis of a liquid sample is provided, which biosensor comprises: a) an insulating base plate having a first end and a second end; b) an electrode system on said insulating base plate, wherein said electrode system comprises a working electrode and a counter electrode, said working and counter electrodes have conductive leads for connecting said electrodes to a readout device for electrochemical measurement on said first end of said base plate, said working electrode is engulfed by said counter electrode on all sides except the side leading to said conductive leads, and there is a gap space between said working and counter electrodes; c) a reaction area as part of said electrode system, said reaction area occupies at least a portion of said working electrode, said counter electrode and the gap space between said working electrode and said counter electrode in a direction perpendicular to said conductive leads, said reaction area is a complete cross-section of said electrode system in a direction perpendicular to said conductive leads, said reaction area is defined by covering the non-reaction-area with a layer comprising a dielectrical material, and said reaction area comprises an enzyme that catalyzes a reaction involving an analyte to be analyzed or a substrate that is involved in a reaction catalyzed by an enzyme to be analyzed; and d) a sample application and reaction chamber, wherein the bottom of said chamber is said reaction area defined in c), the top of said chamber is a cover that covers at least said reaction area, said top has an opening above said reaction area for sample application, the two side walls of said chamber in a direction perpendicular to said conductive leads are formed by said layer comprising said dielectrical material defined in c), and the two sides of said chamber in a direction parallel to said conductive leads are left open as air vents.

In another specific embodiment, a method for assaying an analyte or an enzyme in a liquid sample is provided, which method comprises: a) contacting a liquid sample containing or suspected of containing an analyte or an enzyme with the above-described biosensor in the presence of a suitable electron transfer mediator under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator, leads to the generation of a current that is capable of being detected by the biosensor; and b) detecting the current generated in step a), whereby the presence or amount of the analyte or enzyme in the sample liquid is assessed.

In another aspect, the present invention provides for a biosensor by which the distribution of sample fluid can be ensured to cover all destined reaction area. The biosensor is of particular utility for use in an electrochemical sensor for measuring viscous sample fluids such as whole blood or samples containing large molecules.

In a specific embodiment, a biosensor for electrochemical analysis of a liquid sample is provided, which biosensor comprises: a) an insulating base plate having a first end and a second end; and b) an electrode system on said insulating base plate, wherein said electrode system comprises a working electrode, a counter electrode, and two reference electrodes, said working, counter and reference electrodes have conductive leads for connecting said electrodes to a readout device for electrochemical measurement on said first end of said base plate, each of said reference electrode is diagonally positioned from said working or counter electrode and there is a gap space between said working/counter, working/reference and reference/reference electrodes, said working electrode and a first reference electrode diagonally positioned from said working electrode forms a first closed circuit and said counter electrode and a second reference electrode diagonally positioned from said counter electrode forms a second closed circuit, said first and second closed circuits are connected to form a third circuit, whereby said third circuit is closed only when both said first and second circuits are closed at the same time.

In another specific embodiment, a method for assaying an analyte or an enzyme in a liquid sample is provided, which method comprises: a) providing the above-described biosensor, wherein at least a portion of the working, counter and reference electrodes and the gap space among the electrodes form a reaction area, said reaction area comprises an enzyme that catalyzes a reaction involving an analyte to be analyzed or a substrate that is involved in a reaction catalyzed by an enzyme to be analyzed; b) contacting a liquid sample containing or suspected of containing an analyte or an enzyme with the biosensor containing the enzyme or substrate in the presence of a suitable electron transfer mediator under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator, leads to the generation of a current that is capable of being detected by the biosensor; and c) detecting the current generated in step a), whereby the presence or amount of the analyte or enzyme in the sample liquid is assessed.

BRIEF DESCRIPTION OF THE FIGURES

FIG. 1A illustrates insulating base plate containing an electrode system. FIG. 1B illustrates a dielectric layer covering non-reaction area and leaving non-covered area as the reaction area. FIG. 1C illustrates a top lamina having an opening for sample application.

FIG. 3 illustrates possible configurations of a reaction chamber of an exemplary invention biosensor. 3A: reaction wedge; 3B: reaction tetrahedron; and 3C: reaction trapezohedron.

FIG. 7 is a schematic top view of an exemplary invention biosensor—*Blood Sucker*. FIG. 7A illustrates the loading direction of blood. FIG. 7B illustrates the top laminar with the glue area and the punched hole. FIG. 7C illustrates the addition of two more layers of dielectric materials on the sample loading side.

FIG. 8 is a schematic top view of an exemplary invention biosensor—*Blood Sucker*. FIG. 8A illustrates insulating base plate containing an electrode system. FIG. 8B illustrates a dielectric layer covering non-reaction area and leaving non-covered area as the reaction area. FIG. 8C illustrates the addition of two more layers of dielectric materials and the removal of the dielectric material from the middle portion on the sample loading side.

FIG. 9 is a schematic top view of an exemplary invention biosensor—*Blood Sucker*. FIG. 9A illustrates insulating base plate containing an electrode system. FIG. 9B illustrates a dielectric layer covering non-reaction area and leaving non-covered area as the reaction area.

FIG. 10 is a schematic top view of an exemplary invention biosensor—*Blood Sucker*. FIG. 10A illustrates the loading direction of blood. FIG. 10B illustrates the top laminar with the glue area and the punched hole. FIG. 10C illustrates the addition of two more layers of dielectric materials and the removal of the dielectric material from the middle portion on the sample loading side.

DETAILED DESCRIPTION OF THE INVENTION

A. Definitions

Figure 1:
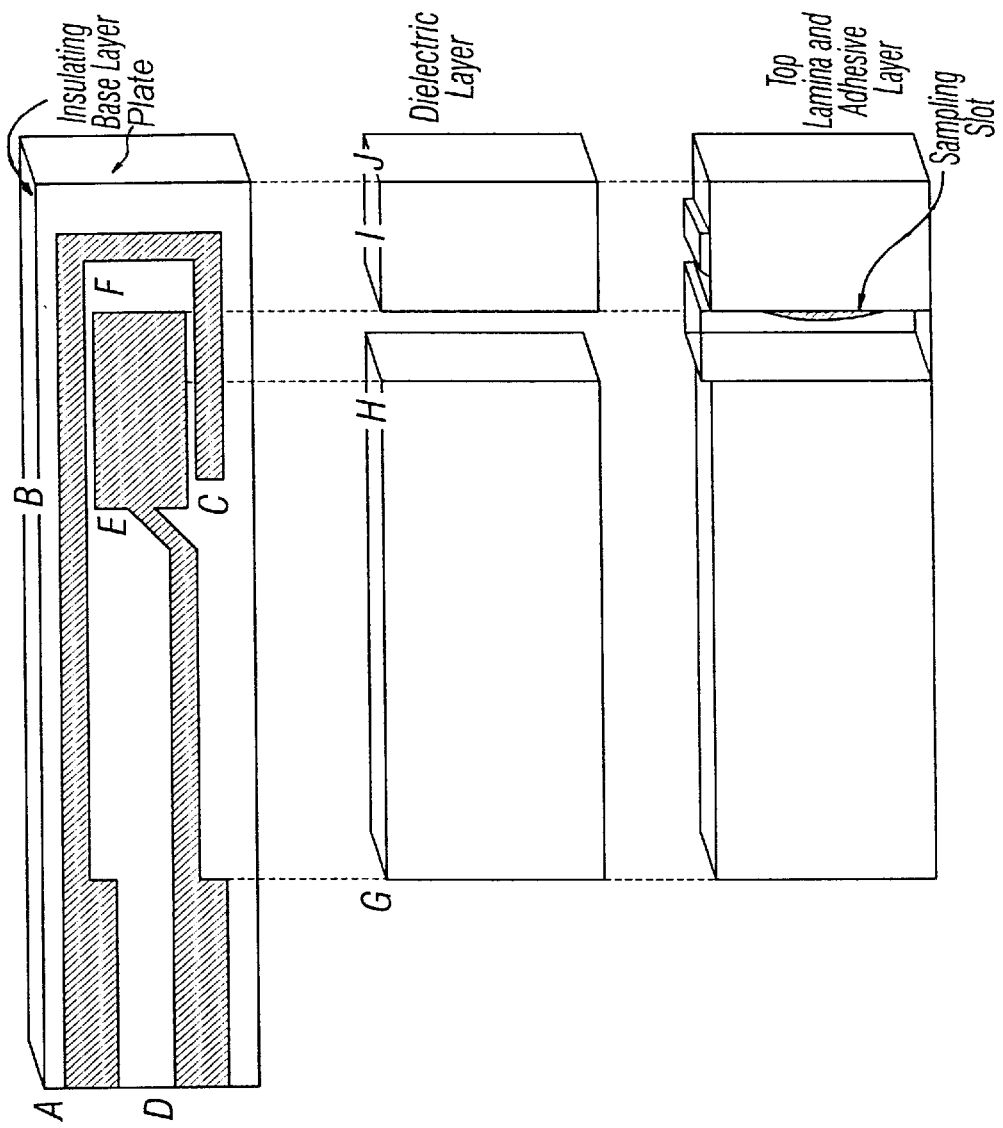
FIG. 1 is a schematic top view of an exemplary invention biosensor.

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, "a direction perpendicular to said conductive leads" refers to a direction which is substantially non-opposing or substantially nonlinear to the direction of the conductive leads. Ordinarily, the angle between the direction perpendicular to the conductive leads and the direction of the conductive leads is from about 45 degrees to about 135 degrees. Preferably, the angle between the two directions is from about 80 degrees to about 100 degrees. More preferably, the angle between the two directions is from about 85 degrees to about 95 degrees. Most preferably, the angle between the two directions is about, or is, 90 degrees.

As used herein, "a direction parallel to said conductive leads" refers to a direction which is substantially opposing or linear to the direction of the conductive leads. Ordinarily, the angle between the direction parallel to the conductive leads and the direction of the conductive leads is about 0–45 degrees or 135–180 degrees. Preferably, the angle between the two directions is about 0–10 degrees or 170–180 degrees. More preferably, the angle between the two directions is 0–5 degrees or 175–180 degrees. Most preferably, the angle between the two directions is about, or is, 0 or 180 degrees.

As used herein, an "enzyme that catalyzes a reaction involving an analyte to be analyzed" refers to an enzyme that directly or indirectly oxidizes or reduces the analyte to be analyzed whereby the oxidization or reduction, in conjunction with an electron transfer mediator either as part of the biosensor or is added during the assay, leads to the generation of a current that is capable of being detected by the biosensor. Preferably, the enzyme uses the analyte as an immediate substrate in its catalyzed oxidizing or reducing reaction. For example, if the analyte to be analyzed is glucose, the enzyme can be an glucose oxidase.

As used herein, a "substrate that is involved in a reaction catalyzed by an enzyme to be analyzed" refers to a substrate that is directly or indirectly used in an oxidizing or reducing reaction catalyzed by an enzyme to be analyzed whereby the oxidization or reduction, in conjunction with an electron transfer mediator either as part of the biosensor or is added during the assay, leads to the generation of a current that is capable of being detected by the biosensor. Preferably, the substrate is as an immediate substrate in the oxidizing or reducing reaction catalyzed by an enzyme to be analyzed. For example, if the enzyme to be analyzed is a glucose oxidase, the substrate can be glucose.

As used herein, "working and counter electrodes are made of substantially identical material(s)" means that identical or nearly identical material(s) are used in both working and counter electrodes so that both electrodes have identical or nearly identical electron transfer properties. Ordinarily, the difference of the electron transfer properties between the two electrodes is less than 50%. Preferably, the difference of the electron transfer properties between the two electrodes is less than 10%. More preferably, the difference of the electron transfer properties between the two electrodes is less than 1%. Most preferably, the working and counter electrodes are made of identical material(s) and there is no difference in their electron transfer properties.

As used herein, "the gap space between the working electrode and the counter electrode is kept substantially constant" means that difference of the gap space between the working electrode and the counter electrode is sufficiently small so that when the working and counter electrodes are made of substantially identical material(s) and have substantially identical surface area, the difference of the gap space between the working electrode and the counter electrode, if there is any, would not affect the uniformity of the electrode performance. Ordinarily, the difference of the gap space between the working electrode and the counter electrode is less than 50%. Preferably, the difference of the gap space is less than 10%. More preferably, the difference of the gap space is less than 1%. Most preferably, the gap space between the working electrode and the counter electrode is kept constant.

As used herein, "the surface area of the working electrode is substantially identical to the surface area of the counter electrode" means that the difference of the surface area between the working electrode and the counter electrode is sufficiently small so that when the working and counter electrodes are made of substantially identical material(s) and the gap space between the working electrode and the counter electrode is kept substantially constant, the difference of the surface area between the working electrode and the counter electrode, if there is any, would not affect the uniformity of the electrode performance. Ordinarily, the difference of the surface area between the working electrode and the counter electrode is less than 50%. Preferably, the difference of the surface area is less than 10%. More preferably, the difference of the surface area is less than 1%. Most preferably, the surface area of the working electrode is identical to the surface area of the counter electrode.

As used herein, "the thickness of the dielectrical material proximal to the first end is substantially higher than the thickness of the dielectrical material proximal to the second end" means that height difference between the sample application site (or the end of the reaction area proximal to the sample application site) and the end of the reaction area distal to the sample application site is sufficient to promote fast and uniform sample liquid flow. Ordinarily, the thickness of the dielectrical material proximal to the first end is at least 1.5 times, but less than 5 times of the thickness of the dielectrical material proximal to the second end. Preferably, the thickness of the dielectrical material proximal to the first end is about three times of the thickness of the dielectrical material proximal to the second end.

As used herein, "the thickness of the dielectrical material of the two corner portions substantially higher than the thickness of the dielectrical material of the middle portion" means that, in the biosensor having the "T-shaped" reaction area, the height difference between the sample application site (or the end of the reaction area proximal to the sample application site) and the end of the reaction area distal to the sample application site and the two corner portions of the non-reaction area proximal to the sample application site is sufficient to promote fast and uniform sample liquid flow. Ordinarily, the thickness of the two corner portions of the non-reaction area proximal to the sample application site is at least 1.5 times, but less than 5 times of the thickness of the dielectrical material of the middle portion of the reaction area that is proximal to the sample application site. Preferably, the thickness of the dielectrical material proximal to the first end and the thickness of the two corner portions proximal to the second end is about three times of a unit thickness and the thickness of the dielectrical material of the middle portion proximal to the second end is about one time of the unit thickness.

As used herein, "working, counter and reference electrodes are made of substantially identical material(s)" means that identical or nearly identical material(s) are used in working, counter and reference electrodes so that the electrodes have identical or nearly identical electron transfer properties. Ordinarily, the difference of the electron transfer properties among the electrodes is less than 50%. Preferably, the difference of the electron transfer properties among the electrodes is less than 10%. More preferably, the difference of the electron transfer properties among the electrodes is less than 1%. Most preferably, the working, counter and reference electrodes are made of identical material(s) and there is no difference in their electron transfer properties.

As used herein, "the gap space between the reference electrodes and the working or counter electrode is kept substantially constant" means that difference of the gap space between the reference electrodes and the working or counter electrode is sufficiently small so that when the working, counter and reference electrodes are made of substantially identical material(s) and the working and counter electrodes have substantially identical surface area, the difference of the gap space between the reference electrodes and the working or counter electrode, if there is any, would not affect the uniformity of the electrode performance. Ordinarily, the difference of the gap space between the reference electrodes and the working or counter electrode is less than 50%. Preferably, the difference of the gap space is less than 10%. More preferably, the difference of the gap space is less than 1%. Most preferably, the gap space between the reference electrodes and the working or counter electrode is kept constant.

As used herein the term "assessing (or assessed)" is intended to include quantitative and qualitative determination in the sense of obtaining an absolute value for the amount or concentration of the analyte or enzyme, e.g., a protein or nucleic acid, present in the sample, and also of obtaining an index, ratio, percentage, visual or other value indicative of the level of analyte or enzyme in the sample. Assessment may be direct or indirect and the chemical species actually detected need not of course be the analyte or enzyme itself but may for example be a derivative thereof or some further substance.

As used herein, "macromolecule" refers to a molecule that, without attaching to another molecule, is capable of generating an antibody that specifically binds to the macromolecule.

As used herein, "small molecule" refers to a molecule that, without forming homo-aggregates or without attaching to a macromolecule or adjuvant, is incapable of generating an antibody that specifically binds to the small molecule. Preferably, the small molecule has a molecular weight that is about or less than 10,000 daltons. More preferably, the small molecule has a molecular weight that is about or less than 5,000 dalton.

As used herein, "vitamin" refers to a trace organic substance required in certain biological species. Most vitamins function as components of certain coenzymes.

As used herein, "lipid" refers to water-insoluble, oily or greasy organic substances that are extractable from cells and tissues by nonpolar solvents, such as chloroform or ether.

As used herein, a "receptor" refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants such as on viruses, cells, or other materials, drugs, polynucleotides, nucleic acids, peptides, cofactors, lectins, sugars, polysaccharides, cells, cellular membranes, and organelles.

As used herein, "antibody" includes antibody fragments, such as Fab fragments, which are composed of a light chain and the variable region of a heavy chain. Antibody encompasses polyclonal and monoclonal antibody.

As used herein, "nutrient or storage protein" refers to a protein that is used by the cell as the nutrient source or storage form for such nutrient. Non-limiting examples of nutrient or storage proteins include gliadin, ovalbumin, casein, and ferritin.

As used herein, "contractile or motile protein" refers to a protein that endows cells and organisms with the ability to contract, to change shape, or to move about. Non-limiting examples of contractile or motile proteins include actin, myosin, tubulin and dynein.

As used herein, "structural protein" refers to a protein that serves as supporting filaments, cables, or sheets to give biological structures strength or protection. Non-limiting examples of structural proteins include keratin, fibroin, collagen, elastin and proteoglycans.

As used herein, "defense protein" refers to a protein that defends organisms against invasion by other species or protect them from injury. Non-limiting examples of defense proteins include antibodies, fibrinogen, thrombin, botulinus toxin, diphtheria toxin, snake venoms and ricin.

As used herein, "regulatory protein" refers to a protein that helps regulate cellular or physiological activity. Non-limiting examples of regulatory proteins include insulin, growth hormones, corticotropin and repressors.

As used herein, "sample" refers to anything which may contain an analyte or enzyme for which an analyte or enzymatic assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The sample may also be a mixture of target analyte or enzyme containing molecules prepared in vitro.

As used herein, a "liquid sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

As used herein, "expressed in a tissue or organ specific manner" refers to a gene expression pattern in which a gene is expressed, either transiently or constitutively, only in certain tissues or organs, but not in other tissues or organs.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein, "plant" refers to any of various photosynthetic, eucaryotic multi-cellular organisms of the kingdom Plantae, charact containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1$\mu$m) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, "disease or disorder" refers to a pathological condition in an organism resulting from, e.g., infection or genetic defect, and characterized by identifiable symptoms.

As used herein, "infection" refers to invasion of the body of a multi-cellular organism with organisms that have the potential to cause disease.

As used herein, "infectious organism" refers to an organism that is capable to cause infection of a multi-cellular organism. Most infectious organisms are microorganisms such as viruses, bacteria and fungi.

As used herein, neoplasm (neoplasia) refers to abnormal new growth, and thus means the same as tumor, which may be benign or malignant. Unlike hyperplasia, neoplastic proliferation persists even in the absence of the original stimulus.

As used herein, cancer refers to a general term for diseases caused by any type of malignant tumor.

For clarity of disclosure, and not by way of limitation, the detailed description of the invention is divided into the subsections that follow.

B. Biosensors Containing a Sample and Reaction Chamber and Methods Using the Same In one aspect, the present invention is directed to a biosensor for electrochemical analysis of a liquid sample, which biosensor comprises: a) an insulating base plate having a first end and a second end; b) an electrode system on said insulating base plate, wherein said electrode system comprises a working electrode and a counter electrode, said working and counter electrodes have conductive leads for connecting said electrodes to a readout device for electrochemical measurement on said first end of said base plate, said working electrode is engulfed by said counter electrode on all sides except the side leading to said conductive leads, and there is a gap space between said working and counter electrodes; c) a reaction area as part of said electrode system, said reaction area occupies at least a portion of said working electrode, said counter electrode and the gap space between said working electrode and said counter electrode in a direction perpendicular to said conductive leads, said reaction area is a complete cross-section of said electrode system in a direction perpendicular to said conductive leads, said reaction area is defined by covering the non-reaction-area with a layer comprising a dielectrical material, and said reaction area comprises an enzyme that catalyzes a reaction involving an analyte to be analyzed or a substrate that is involved in a reaction catalyzed by an enzyme to be analyzed; and d) a sample application and reaction chamber, wherein the bottom of said chamber is said reaction area defined in c), the top of said chamber is a cover that covers at least said reaction area, said top has an opening above said reaction area for sample application, the two side walls of said chamber in a direction perpendicular to said conductive leads are formed by said layer comprising said dielectrical material defined in c), and at least a portion of the two sides of said chamber in a direction parallel to said conductive leads are left open as air vents.

The biosensor can be in any suitable shapes such as rectangle, square, circle, oval or other regular or irregular shapes. Preferably, the biosensor is a rectangle.

The insulating base plate can be made of any suitable material(s). Preferably, the insulating base plate comprises vinyl polymer(s), polymide(s), polyester(s), nylon, nitrocellulose or a combination thereof.

The working and counter electrodes can be made of any suitable material(s). Although not required, the working and counter electrodes are preferably made of substantially identical material(s) within the reaction area. More preferably, the working and counter electrodes are made of identical material(s) within the reaction area. Most preferably, the working and counter electrodes are made of identical material(s) throughout the entire biosensor.

The gap space between the working electrode and the counter electrode can be kept constant or can be varied. Preferably, the gap space between the working electrode and the counter electrode is kept substantially constant within the reaction area. More preferably, the gap space between the working electrode and the counter electrode is kept constant within the reaction area. Most preferably, the gap space between the working electrode and the counter electrode is kept constant throughout the entire biosensor.

The width of the working electrode can be identical to or different from the width of the counter electrode within the reaction area. In a preferred embodiment, the width of the working electrode is about twice of the width of the counter electrode within the reaction area.

The surface area of the working electrode can be identical to or different from the surface area of the counter electrode. Preferably, the surface area of the working electrode is substantially identical to the surface area of the counter electrode within the reaction area. More preferably, the surface area of the working electrode is identical to the surface area of the counter electrode within the reaction area. Most preferably, the surface area of the working electrode is identical to the surface area of the counter electrode throughout the entire biosensor.

In a preferred embodiment, the working and counter electrodes are made of identical material(s) within the reaction area, the gap space between the working electrode and the counter electrode is kept constant within the reaction area, and the surface area of the working electrode is identical to the surface area of the counter electrode within the reaction area.

The electrode system can be placed or made onto the insulating base plate by any suitable methods known in the art. For example, electrodes can be unrolled from reels and attached to the insulating base plate using hot melt adhesive. Preferably, the electrode system is screen-printed onto the insulating base plate. When the electrode system is screen-printed onto the insulating base plate, the working and counter electrodes can comprise carbon paste and the conductive leads can comprise conductive silver paste. The electrode system can also be placed or made onto the insulating base plate by the methods disclosed in the following literatures: Kureishi et al., *Bioelectrochem. Bioenerg.*, 48(1):95–100 (1999); Anzai et al., *Anal. Chem.*, 70(4):811–7 (1998); and Stonehuemer et al., *Biosens. Bioelectron.*, 7(6):421–8 (1992).

The reaction area can be defined by covering the non-reaction-area with a layer comprising a dielectrical material. Any suitable dielectrical material can be used. Preferably, the dielectrical material used in the biosensor is vinylpolyester(s), polyimide(s) or a combination thereof.

To ensure quick and uniform distribution of sample liquid, especially small volume of sample liquid, the thickness of the dielectrical material proximal to the first end should be substantially higher than the thickness of the dielectrical material proximal to the second end. Preferably, the thickness of the dielectrical material proximal to the first end is about three times of the thickness of the dielectrical material proximal to the second end.

The top of the sample application and reaction chamber must cover at least the entire reaction area. Preferably, the biosensor has a cover that covers the surface of the entire biosensor and the top of the sample application and reaction chamber is the corresponding part of the cover for the entire biosensor. In one example, the cover for the entire biosensor is a lamina adhered to the non-reaction-area and the opening on the top is a punched hole formed on said lamina. Preferably, the punched hole of the lamina has an arcuate part of the sampling slot protruding into the reaction area to form a convex, said convex serves as the passage for the sample fluid to the reaction area and the arcuate part of the convex provide an auxiliary of propulsion for a quick draw of the sample fluid.

Although not required, the insulating base plate can be transparent, whereby the liquid sample is introduced on the opposite side of the transparent insulating base plate and the liquid sample movement can be monitored through the transparent insulating base plate.

The biosensor can further comprise an electron transfer mediator in the reaction area. Exemplary transfer mediators include ferrocene and its derivatives, osmium complex, tetrathiofulvalene, phenazine ethosulfate, benzoquinone or hexacyanoferrate.

The biosensor can have a "T-shaped" reaction area, wherein the non-reaction area proximal to the second end is divided into two corner portions and one middle portion, and the middle portion is made part of the reaction area by either not covering the middle portion with a layer comprising a dielectrical material or by making the thickness of the dielectrical material of the two corner portions substantially higher than the thickness of the dielectrical material of the middle portion, whereby the reaction area occupies a T-shaped area comprising the complete cross-section in a direction perpendicular to said conductive leads and a strip area in a direction parallel to said conductive leading from the cross-section to the edge of the second end. Preferably, the thickness of the dielectrical material proximal to the first end and the thickness of the two corner portions proximal to the second end is about three times of a unit thickness and the thickness of the dielectrical material of the middle portion proximal to the second end is about one time of the unit thickness.

In another aspect, the present invention is directed to a method for assaying an analyte or an enzyme in a liquid sample, which method comprises: a) contacting a liquid sample containing or suspected of containing an analyte or an enzyme with the above-described biosensor in the presence of a suitable electron transfer mediator under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator, leads to the generation of a current that is capable of being detected by the biosensor; and b) detecting the current generated in step a), whereby the presence or amount of the analyte or enzyme in the sample liquid is assessed.

Any suitable volume of a liquid sample can be assayed by the present method. Preferably, the present method is used for assaying a small volume of a liquid sample. For example, the volume of the liquid sample to be assayed is from about 1.5 microliters to about 10.0 microliters. Preferably, the volume of the liquid sample to be assayed is from about 1.5 microliters to about 3.0 microliters.

Any analyte that can be involved in an oxidizing or a reducing reaction or any enzyme that catalyzes an oxidizing or a reducing reaction can be assayed by the present method. For example, the analyte to be detected can be glucose. Preferably, the enzyme comprised in the reaction area of the biosensor is glucose oxidase and the electron transfer mediator used in the assay is potassium ferricyanide.

In a specific embodiment, the present invention is directed to a method for assaying an analyte or an enzyme in a liquid sample, which method comprises: a) contacting a liquid sample containing or suspected of containing an analyte or an enzyme with the above-described biosensor which contains a suitable electron transfer mediator in the reaction area under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator comprised in the reaction area of the biosensor, leads to the generation of a current that is capable of being detected by the biosensor; and b) detecting the current generated in step a), whereby the presence or amount of the analyte or enzyme in the sample liquid is assessed.

In another specific embodiment, the present invention is directed to a method for assaying an analyte or an enzyme in a liquid sample, which method comprises: a) contacting a liquid sample containing or suspected of containing an analyte or an enzyme with the above-described biosensor which contains a "T-shaped" reaction area in the presence of a suitable electron transfer mediator under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator, leads to the generation of a current that is capable of being detected by the biosensor; and b) detecting the current generated in step a), whereby the presence or amount of the analyte or enzyme in the sample liquid is assessed.

C. Biosensors Containing Diagonally Positioned Quadruple Electrodes and Methods Using the Same In one aspect, the present invention is directed to a biosensor for electrochemical analysis of a liquid sample, which biosensor comprises: a) an insulating base plate having a first end and a second end; and b) an electrode system on said insulating base plate, wherein said electrode system comprises a working electrode, a counter electrode, and two reference electrodes, said working, counter and reference electrodes have conductive leads for connecting said electrodes to a readout device for electrochemical measurement on said first end of said base plate, each of said reference electrode is diagonally positioned from said working or counter electrode and there is a gap space between said working/counter, working/reference and reference/reference electrodes, said working electrode and a first reference electrode diagonally positioned from said working electrode forms a first closed circuit and said counter electrode and a second reference electrode diagonally positioned from said counter electrode forms a second closed circuit, said first and second closed circuits are connected to form a third circuit, whereby said third circuit is closed only when both said first and second circuits are closed at the same time.

The biosensor can be in any suitable shapes such as rectangle, square, circle, oval or other regular or irregular shapes. Preferably, the biosensor is a rectangle.

The insulating base plate can be made of any suitable material(s). Preferably, the insulating base plate comprises vinyl polymer(s), polymide(s), polyester(s), nylon, nitrocellulose or a combination thereof.

The working, counter and reference electrodes can be made of any suitable material(s). Although not required, the working, counter and reference electrodes are preferably made of substantially identical material(s) within the reaction area. More preferably, the working, counter and reference electrodes are made of identical material(s) within the reaction area. Most preferably, the working, counter and reference electrodes are made of identical material(s) throughout the entire biosensor.

The gap space between the reference electrodes and the working or counter electrode can be kept constant or can be varied. Preferably, the gap space between the reference electrodes and the working or counter electrode is kept substantially constant within the reaction area. More preferably, the gap space between the reference electrodes and the working or counter electrode is kept constant within the reaction area. Most preferably, the gap space between the reference electrodes and the working or counter electrode is kept constant throughout the entire biosensor.

The surface area of the working electrode can be identical to or different from the surface area of the counter electrode. Preferably, the surface area of the working electrode is substantially identical to the surface area of the counter electrode within the reaction area. More preferably, the surface area of the working electrode is identical to the surface area of the counter electrode within the reaction area. Most preferably, the surface area of the working electrode is identical to the surface area of the counter electrode throughout the entire biosensor.

In a preferred embodiment, the working, counter and reference electrodes are made of identical material(s) within the reaction area, the gap space between the reference electrodes and the working or counter electrode is kept constant within the reaction area, and the surface area of the working electrode is identical to the surface area of the counter electrode within the reaction area.

The electrode system can be placed or made onto the insulating base plate by any suitable methods known in the art. For example, electrodes can be unrolled from reels and attached to the insulating base plate using hot melt adhesive. Preferably, the electrode system is screen-printed onto the insulating base plate. When the electrode system is screen-printed onto the insulating base plate, the working, counter and reference electrodes can comprise carbon paste and the conductive leads can comprise conductive silver paste. The electrode system can also be placed or made onto the insulating base plate by the methods disclosed in the following literatures: Kureishi et al., *Bioelectrochem. Bioenerg.*, 48(1):95–100 (1999); Anzai et al., *Anal. Chem.*, 70(4):811–7 (1998); and Stonehuemer et al., *Biosens. Bioelectron.*, 7(6):421–8 (1992).

Figure 6A:
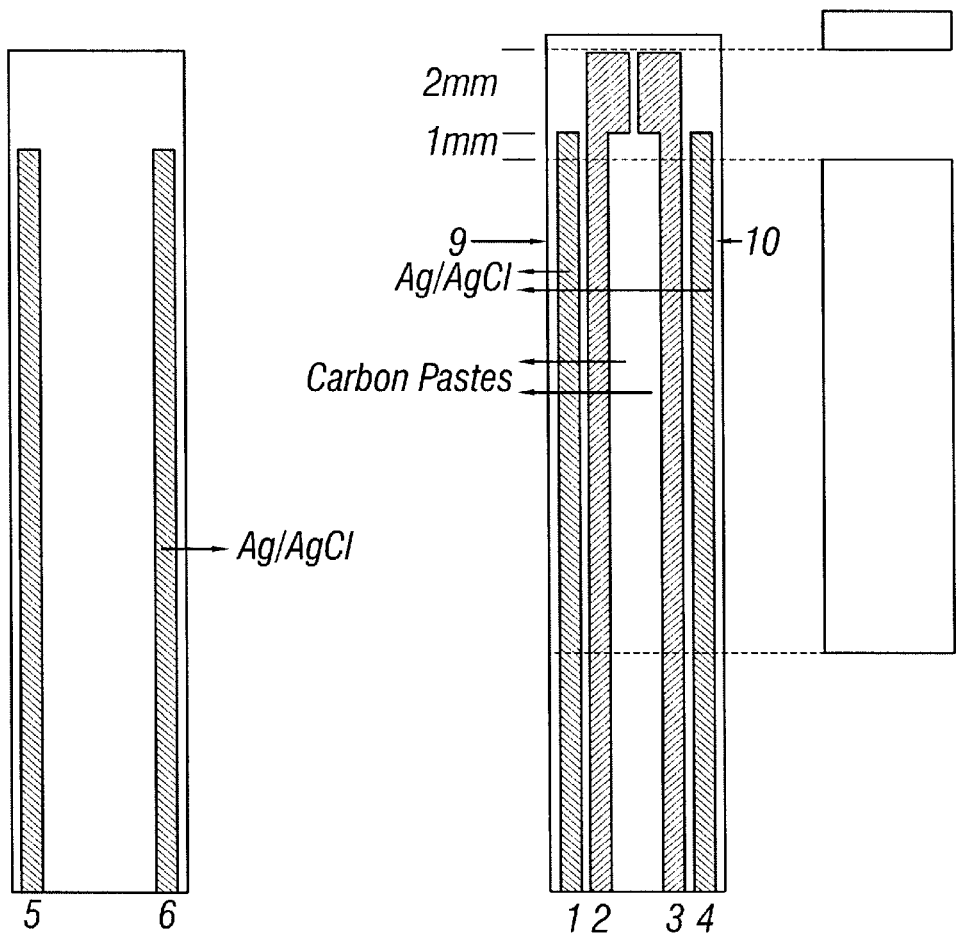
FIG. 6 illustrates another exemplary invention biosensor containing diagonally positioned quadruple electrodes. 6A: top view; and 6B: circuit connections of the quadruple electrodes.
Figure 6B:
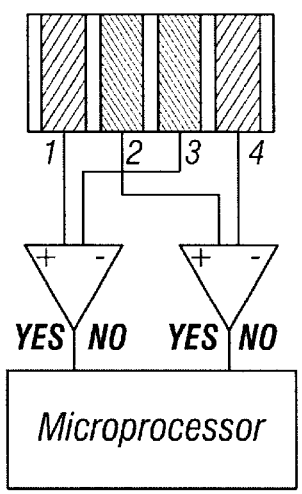

The working, counter and reference electrodes can be arranged in any suitable fashion. Preferably, the reference electrodes are engulfed by the working and counter electrodes on all sides except the side leading to said conductive leads. Also preferably, the reference electrodes are separated to the farthest distance without contacting either working or counter electrode. Alternatively, the reference electrodes can be on the outside and the working and counter electrodes can be on the inside as illustrated in FIG. 6.

The biosensor can further comprise a reaction area, wherein at least a portion of the working, counter and reference electrodes and the gap space among the electrodes form the reaction area, said reaction area comprises an enzyme that catalyzes a reaction involving an analyte to be analyzed or a substrate that is involved in a reaction catalyzed by an enzyme to be analyzed.

The biosensor can further comprise an electron transfer mediator in the reaction area. Exemplary transfer mediators include ferrocene and its derivatives, osmium complex, tetrathiofulvalene, phenazine ethosulfate, benzoquinone or hexacyanoferrate.

The biosensor can further comprise a sample application and reaction chamber, wherein the reaction area is a complete cross-section of the electrode system in a direction perpendicular to the conductive leads, the reaction area is defined by covering the non-reaction-area with a layer comprising a dielectrical material, and the biosensor further comprises a sample application and reaction chamber, wherein the bottom of said chamber is the reaction area, the top of said chamber is a cover that covers at least the reaction area, said top has an opening above the reaction area for sample application, the two side walls of said chamber in a direction perpendicular to said conductive leads are formed by the layer comprising the dielectrical material, and at least a portion of the two sides of said chamber in a direction parallel to said conductive leads are left open as air vents.

The reaction area can be defined by covering the non-reaction-area with a layer comprising a dielectrical material. Any suitable dielectrical material can be used. Preferably, the dielectrical material used in the biosensor is vinylpolyester(s), polyimide(s) or a combination thereof.

To ensure quick and uniform distribution of sample liquid, especially small volume of sample liquid, the thickness of the dielectrical material proximal to the first end should be substantially higher than the thickness of the dielectrical material proximal to the second end. Preferably, the thickness of the dielectrical material proximal to the first end is about three times of the thickness of the dielectrical material proximal to the second end.

The top of the sample application and reaction chamber must cover at least the entire reaction area. Preferably, the biosensor has a cover that covers the surface of the entire biosensor and the top of the sample application and reaction chamber is the corresponding part of the cover for the entire biosensor. In one example, the cover for the entire biosensor is a lamina adhered to the non-reaction-area and the opening on the top is a punched hole formed on said lamina. Preferably, the punched hole of the lamina has an arcuate part of the sampling slot protruding into the reaction area to form a convex, said convex serves as the passage for the sample fluid to the reaction area and the arcuate part of the convex provide an auxiliary of propulsion for a quick draw of the sample fluid.

Although not required, the insulating base plate can be transparent, whereby the liquid sample is introduced on the opposite side of the transparent insulating base plate and the liquid sample movement can be monitored through the transparent insulating base plate.

The biosensor can have a "T-shaped" reaction area, wherein the non-reaction area proximal to the second end is divided into two corner portions and one middle portion, and the middle portion is made part of the reaction area by either not covering the middle portion with a layer comprising a dielectrical material or by making the thickness of the dielectrical material of the two corner portions substantially higher than the thickness of the dielectrical material of the middle portion, whereby the reaction area occupies a T-shaped area comprising the complete cross-section in a direction perpendicular to said conductive leads and a strip area in a direction parallel to said conductive leading from the cross-section to the edge of the second end. Preferably, the thickness of the dielectrical material proximal to the first end and the thickness of the two corner portions proximal to the second end is about three times of a unit thickness and the thickness of the dielectrical material of the middle portion proximal to the second end is about one time of the unit thickness.

In another specific embodiment, a method for assaying an analyte or an enzyme in a liquid sample is provided, which method comprises: a) providing the above-described biosensor, wherein at least a portion of the working, counter and reference electrodes and the gap space among the electrodes form a reaction area, said reaction area comprises an enzyme that catalyzes a reaction involving an analyte to be analyzed or a substrate that is involved in a reaction catalyzed by an enzyme to be analyzed; b) contacting a liquid sample containing or suspected of containing an analyte or an enzyme with the biosensor containing the enzyme or substrate in the presence of a suitable electron transfer mediator under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator, leads to the generation of a current that is capable of being detected by the biosensor; and c) detecting the current generated in step a), whereby the presence or amount of the analyte or enzyme in the sample liquid is assessed.

Any suitable volume of a liquid sample can be assayed by the present method. Preferably, the present method is used for assaying a small volume of a liquid sample. For example, the volume of the liquid sample to be assayed is from about 1.5 microliters to about 10.0 microliters. Preferably, the volume of the liquid sample to be assayed is from about 1.5 microliters to about 3.0 microliters.

Any analyte that can be involved in an oxidizing or a reducing reaction or any enzyme that catalyzes an oxidizing or a reducing reaction can be assayed by the present method. For example, the analyte to be detected can be glucose. Preferably, the enzyme comprised in the reaction area of the biosensor is glucose oxidase and the electron transfer mediator used in the assay is potassium ferricyanide.

In a specific embodiment, the present invention is directed to a method for assaying an analyte or an enzyme in a liquid sample, which method comprises: a) contacting a liquid sample containing or suspected of containing an analyte or an enzyme with the above-described biosensor which contains a suitable electron transfer mediator in the reaction area under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator comprised in the reaction area of the biosensor, leads to the generation of a current that is capable of being detected by the biosensor; and b) detecting the current generated in step a), whereby the presence or amount of the analyte or enzyme in the sample liquid is assessed.

In another specific embodiment, the present invention is directed to a method for assaying an analyte or an enzyme in a liquid sample, which method comprises: a) contacting a liquid sample containing or suspected of containing an analyte or an enzyme with the above-described biosensor which contains a sample application and reaction chamber in the presence of a suitable electron transfer mediator under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator, leads to the generation of a current that is capable of being detected by the biosensor; and b) detecting the current generated in step a), whereby the presence or amount of the analyte or enzyme in the sample liquid is assessed.

In still another specific embodiment, the present invention is directed to a method for assaying an analyte or an enzyme in a liquid sample, which method comprises: a) contacting a liquid sample containing or suspected of containing an analyte or an enzyme with the above-described biosensor which contains a "T-shaped" sample application and reaction chamber in the presence of a suitable electron transfer mediator under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator, leads to the generation of a current that is capable of being detected by the biosensor; and b) detecting the current generated in step a), whereby the presence or amount of the analyte or enzyme in the sample liquid is assessed.

D. Exemplary Uses of the Biosensors and the Assaying Methods

The present biosensors and methods can be used to qualitatively or quantitatively detect any analyte or enzyme. For example, the analyte to be assayed can be macromolecules such as peptides, proteins, e.g., antibodies or receptors, oligonucleotides, nucleic acids, vitamins, oligosaccharides, carbohydrates, lipids, or small molecules, or a complex thereof. Exemplary proteins or peptides include enzymes, transport proteins such as ion channels and pumps, nutrient or storage proteins, contractile or motile proteins such as actins and myosins, structural proteins, defense proteins or regulatory proteins such as antibodies, hormones and growth factors. Exemplary nucleic acids include DNA, such as A-, B- or Z-form DNA, and RNA such as mRNA, tRNA and rRNA. The nucleic acids can be single-, double-and triple-stranded nucleic acids. Exemplary vitamins include water-soluble vitamins such as thiamine, riboflavin, nicotinic acid, pantothenic acid, pyridoxine, biotin, folate, vitamin $B_{12}$ and ascorbic acid, and fat-soluble vitamins such as vitamin A, vitamin D, vitamin E, and vitamin K. Exemplary lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

Preferably, the analyte or enzyme to be detected is a marker for a biological pathway, a stage of cell cycle, a cell type, a tissue type, an organ type, a developmental stage, a disease, disorder or infection type or stage, or drug or other treatments. Exemplary tissues include connective, epithelium, muscle or nerve tissues. Exemplary organs include an accessory organ of the eye, annulospiral organ, auditory organ, Chievitz organ, circumventricular organ, Corti organ, critical organ, enamel organ, end organ, external female gential organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subfornical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl can be manipulated. Exemplary internal animal organs include brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels. Exemplary diseases or disorders include neoplasm (neoplasia), cancers, immune system diseases or disorders, metabolism diseases or disorders, muscle and bone diseases or disorders, nervous system diseases or disorders, signal diseases or disorders, transporter diseases or disorders.

Analyte from any fluid sample can be detected by the present method. Exemplary liquid sample include buffer, blood, serum, plasma, or urine, or a solution or suspension containing solid or gaseous biological material.

E. Preferred Embodiments

1. Exemplary Biosensors Containing a Sample Application and Reaction Chamber

In one specific embodiment, the present invention provides a biosensor, which comprises an electrically insulating base plate, two screen-printed electrodes consisting of a working one and counter one, a reaction layer including at least an oxidoreductase, an electron transfer mediator, and an reaction chamber. The working electrode is formed in the center of reaction area and is surrounded by the counter electrode by a short, uniform distance. The pulse voltage applied to this working electrode activates the electrooxidation of the reduced mediator and the resulting electron flow is transduced as a measurable current signal.

To achieve homogenous and quick reaction, sample loading is facilitated with two devices; a "loading convex" and a "reaction trapezohedron." The two parallel faces of the reaction trapezohedron is created by flanking the reaction area at outer side (to the sample-loading area) with a thin layer of dielectric material and the inner side of the reaction area (to the electrode leads) with the same dielectric material with three times of thickness. The top principal face is formed by covering the chamber with a lamina. The lamina has adhesive material on both ends excluding the rectangular portion over the reaction area. The two trapezoids on the sideways sides of the reaction chamber are left open to the ambient air. A sampling slot is formed by a pouch on the covering lamina.

The upload of sample fluid is eased up by a touch on the sampling slot. An arcuate portion of the slot protrudes into the reaction chamber to form a convex facing the reaction area. This is called a "loading convex" with the purpose to provide auxiliary propulsion by its outward surface tension. The ascending lamina and the two trapezoidous air vents on the sideways provide a pull-up force for the sample fluids. With this special devise, only minute amount of sample volume, e.g., 1.5 microliters, is required for the test. The quick draw of sample fluid, e.g., blood, to the reaction area ensures that a homogenous thin layer of sample fluid to be laid on top of the reaction layer, which ensures a rapid and uniform enzymatic reaction and a subsequent uniform generation of electronic flow.

Another aspect of this invention is that sampling slot can be located on the bottom side of the sensors. On the top side, the front portion of the sensors is made transparent to serve as window for locating the sample fluid, for instance, a puncture in the fingerstick, and for monitoring the movement of the fluid. Sample introduction through this bottomside slot is with much ease and the amount of introduced volume can be sure to cover the whole reaction layer. It is also another benefit of this design to be able to pick up samples form alternative sites such as punctures at body parts other than fingersticks. Forearms, containing fewer nerves, can be the alternative sites for blood withdrawal with less pain. The special design of this invention has been shown to take in blood from forearms with ease.

Figure 4A:
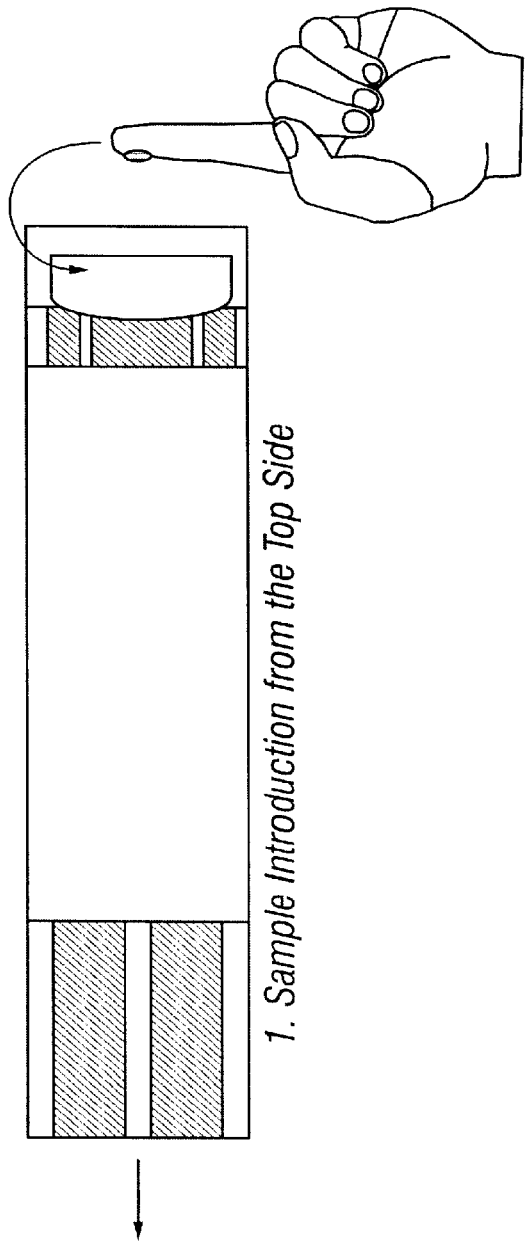
FIG. 4 illustrates top and reverse view of sample application on an exemplary invention biosensor. 4A: top view; and 4B: reverse view.
Figure 4B:
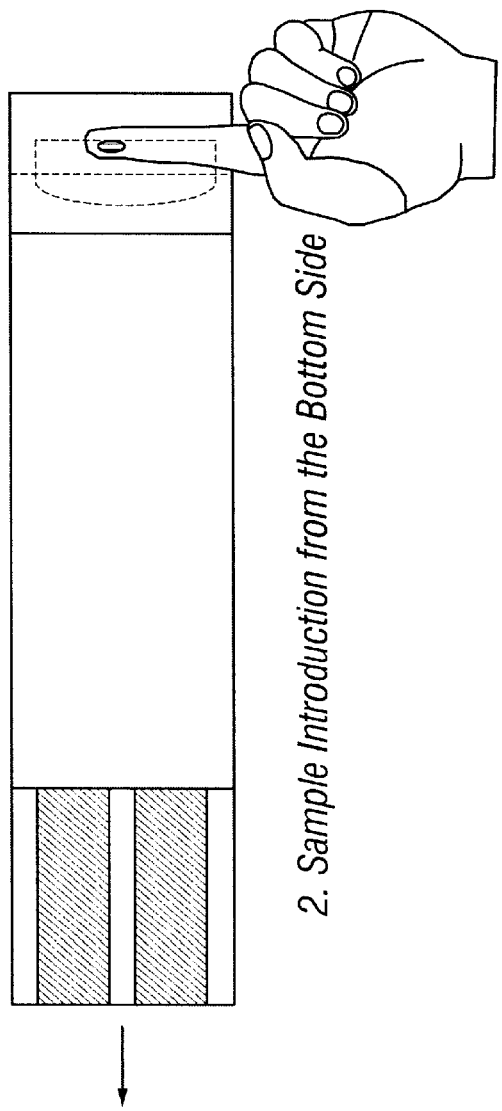

It is found that in the conventional method of introducing blood from fingersticks, the punctured fingerstick has to be located right on top of the sampling slot for the droplet of blood to be put into slot. This usually blocks the vision of the slot and thus frequently hinders a successful introduction of blood samples. It is even more handicapped for poor bleeders to be able to apply their scant blood by this method. In this invention, it is still another aspect that the sample fluid introduction can be done through the bottom side of the biosensor. As shown in FIG. 4, sample introduction can be through the sampling slot locating on the bottom side of the biosensor. A window is left transparent in the front portion of the strip on the top side, a better location of the puncture in fingerstick and a clear vision of the movement of the sample fluids can be accomplished.

In the above-mentioned biosensor, the reaction layer practically contains a reagent mixture containing oxidoreductase, electron transfer mediator, and an electrode system. Sample fluid is loaded into the slot and is immediately drawn to the reaction area with the help of the loading convex and a reaction trapezohedron. In a very short time, the reagent dissolves and the enzymatic reaction proceeds. At the completion of enzymatic reaction, a controlled-potential is applied between the electrodes to trigger another round of electrooxidation. After a short time delay, the electronic flow produced by the electrooxidation of the reduced mediator is measured and correlated to the presence or amount of the analyte in the sample fluid.

A glucose sensor will be described hereinafter as one example of the invention biosensor. FIG. 1 is a schematic top view of the screen-printed electrode system of this inventive biosensor. The electrode system is made by screen-printing two silver pastes as lead-conductors and subsequently two conductive carbon pastes. The conductive silver paste AB and carbon paste BC form the counter electrode and silver paste DE and carbon paste EF form the working one. The diffusion gap between the working and the counter electrodes all around the reaction area is uniformly to be 0.5 mm microns and the working electrode encompassed by counter electrode on all sides except the side to the direction to the lead conductors. This configuration facilitates the maximum electrode performance. The electrodes are then covered by dielectrical material (area GH and IJ) excluding the meter-contact leads and the reaction area HI. The reaction area on the electrodes is defined to be 10 mm$^2$ (=5 mm×2 mm). Within the reaction area, the surface area of the working electrode is 4 mm$^2$(=2 mm×2 mm), which equals to the sum of two counter ones (=2×1 mm×2 mm). Both electrodes in the reaction area are made of the same electrically conducting material (carbon paste in this case). Layer 3 refers to the covering lamina with two adhesive ends and a punched hole serving as sampling slot. When the lamina is laid upon the dielectric layer, a chamber of trapezohedron is formed. The two trapezoids on the sideways sides of the strip are open to the ambient air and serve as air vents.

Figure 2:
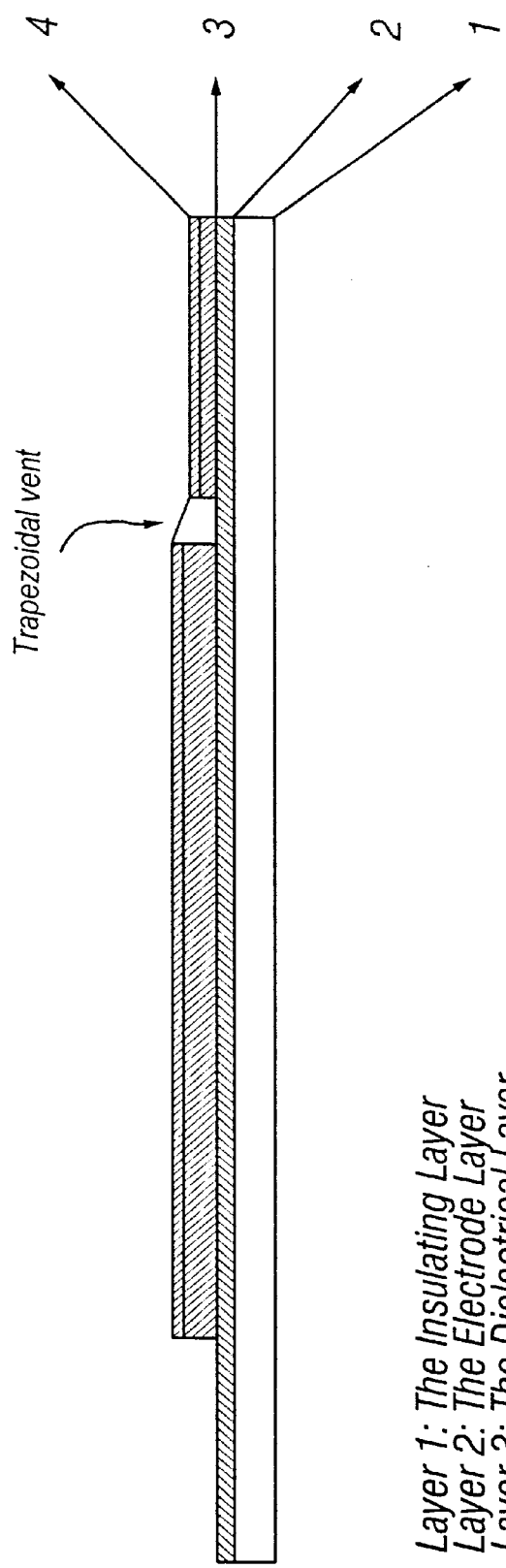
FIG. 2 is a cross-sectional view of an exemplary invention biosensor. Layer 1: the insulating layer; Layer 2: the electrode layer; Layer 3: the dielectrical layer; and Layer 4: the covering lamina.

The cross-sectional view of the embodiment of this inventive biosensor excluding the reagent is shown in FIG. 2. Layer 1 is the insulating base substrate with a thickness of 0.5 mm. The insulting layer may be of any useful thickness and of any material as long as it meets the requirement of rigidity for mass production and user's convenience. Layer 2 is the electrode layer mentioned in the previous paragraph.

Dielectric layer 3 is screen-printed onto the insulating base. Any useful insulating material, such as vinyl polymers and polyimides, providing the electrical and structure properties, will be suitable as the dielectric material. The other feature of this dielectrical covering is that the thickness of these two coating layers are uneven, with the thickness on the reaction side (90–150 microns) is three-time larger than that of the sample-loading side (30–50 microns). A lamina layer (Layer 4) with two adhesive ends is then put on top of the dielectric layer to form a trapezohedron as the reaction chamber. The sampling slot is a punched hole on the lamina.

Two important features of this invention biosensor, reaction trapezohedron and loading convex, are shown in the third graph in FIG. 3. With the thickness of the lamina being 2 mm, the sampling slot is a depression capable of serving as reservoir for sample fluids. An arcuate portion of this slot overlaps and protrudes the reaction area to form a convex facing reaction layer. This loading convex provides auxiliary propulsion for the sample introduction with its outward surface tension. Since only this arcuate portion is left unsealed, it also serves as the only passage for the sample loading. The loaded sample fluid thus can only go unilaterally through the arcuate passage and no sample is wasted on non-reaction area. When the loaded sample fluids pass the loading convex, they are pulled upwardly and forwardly to fill the reaction layer with no hesitation. The pull-up forces are from the adhesion of the fluids and the covering lamina and the cohesion of the fluids themselves. The sideways trapezoids provide the necessary air vents for this pull-up function.

The advantages of this embodiment are two-folded. First, a minute amount of sample fluid, e.g., 1.5 microliters, is required for the test. Second, the quick and effective drawing of blood over the reaction area generates a homogenous enzymatic reaction and a uniformly diffusion-dependent electrochemical reaction.

An experiment is therefore designed to test the efficiency of the "loading convex" and "reaction trapezohedron" to introduce sample into the reaction layer. When an aqueous sample is successfully introduced to the reaction area of a biosensor, a glucose meter is able to detect a change of current from the chemical reaction and proceeds the test. According to a glucose meter, e.g., GlucoSure, from Apex Biotechnology Co. (Taiwan), the successful sample introduction can be indicated by a beep sound to show a detection of the initial chemical reaction. A lag for the occurrence of the beep sound can thus be used to measure the "dose hesitation," a delay in sample introduction. Three different types of sample introducing devices shown in FIG. 3 have been tested; device 1 is a reaction chamber without sideways air vents and loading convex (graph 1), device 2 is a reaction tetrahedron (graph 2) with two rectangular sideways faces as air vents, and device 3 is a reaction trapezohedron (graph 3). The result is shown in the following Table 1. Dose hesitation as a lag of the introduction of sample fluid, was evidenced in both the reaction tetrahedron and the reaction chamber without air vents and loading convex. With ten samples from each design (N=10), the frequency of the appearance of dose hesitation was 100% for the design 1 and was 40% for the second design. No such dose hesitation was found in reaction trapezohedron.

TABLE 1

The result of dose hesitation in three devices for sample introduction

| Dose hesitation (in seconds) | Device 1 | Device 2 | Device 3 |
|---|---|---|---|
| 1 | 11.65 | 11.65 | 0 |
| 2 | 12.08 | 12.08 | 0 |
| 3 | 28.55 | 28.55 | 0 |
| 4 | 6.13 | 6.13 | 0 |
| 5 | 0 | 0 | 0 |
| 6 | 6.56 | 6.56 | 0 |
| 7 | 0 | 0 | 0 |
| 8 | 48.47 | 48.47 | 0 |
| 9 | 66.61 | 66.61 | 0 |
| 10 | 62.23 | 62.23 | 0 |

Before covering lamina is applied, the reaction chemicals including glucose oxidase (referred to as GOD hereinafter) as an oxidoreductase and potassium ferricyanide, $K_3Fe(CN)_6$ as electron transfer mediator were prepared in a preparation buffer. The preparation buffer is a 0.4 M phosphate buffer (pH=7.0) with 0.1% Triton X-100 as surfactant. A volume of 3 microliter of reagent was dispensed onto the reaction layer, air-dried for 30 minutes with 45% humidity before moved into the dry room for further drying. As a result, a uniform reaction layer was formed. The test started with an introduction of sample fluid and the concentration of glucose was measured as the current generated through the electrooxidation.

Another way of making the invention biosensor is illustrated in FIGS. 7–10. As shown in FIGS. 7–10, instead of making one layer (e.g., thickness about 0.25 mm) of dielectric material on the sample loading side, two more layers (e.g., thickness 0.25×2) of dielectric materials can be screen-printed on this area as shown in the FIGS. 7–10 to leave a trench-like or "T-shaped" sample transferring passage. Since the above-described reaction area is defined as the rectangular area by the printed dielectric materials, reagents are restrained and cannot be overflowed during the sample application. A top laminar with a punched hole and specially designed glue area is then put on top of the above-described electrode plate. A pouch on the above-described electrode plate thus yields the biosensor. In this specially designed biosensor, the transferring path for the sample fluid is a T-shaped trench and the two air vents are left open on the two ends of the crossbar of the T-trench. On the front for sample loading, a convex connected to vertical bar of the T-trench serves as the sample loading area. A quick and uniform application of sample fluid is made possible. This aspect also makes the manufacturing process of the biosensors simple.

Although the foregoing descriptions are all related to an amperometric glucose biosensor, this invention is widely applicable to an enzyme-related system such as cholesterol sensor, alcohol sensor, lactate sensor, etc. As mentioned above, the biosensor of the invention is capable of measuring a specific component in various kinds of samples rapidly. Moreover, the manufacturing process of present invention enables mass production of the biosensor strips with fairly simple procedures, low costs, and large volume of production.

2. Exemplary Biosensors Containing Diagonally Positioned Quadruple Electrodes

The invention also features a biosensor having four electrodes: one working electrode, one counter electrode, and two reference electrodes, preferably screen-printed on an insulating substrate. The working electrode and the counter electrode can be made of the same materials and with the same size. They are spaced from each other with a short and uniform distance, so a homogenous diffusion of chemicals and electronic transfer can be ensured. An enzyme of the capacity to catalyze the analyte can be added on the above-mentioned electrodes. A mediator can also be added on this area as an electron trapper for the electrochemical reaction. The sample fluid containing the analyte is applied from the front end of the electrode strip and the current generates on the working electrode after the enzymatic and electrochemical reaction can be measured and correlated to the presence or concentration of the analyte.

Two reference electrodes are located downstream of the sample transfer path. They are made of the same materials and with the same size. These two electrodes are separated to the farthest distance without contacting with either working or counter electrode. In such an arrangement, one of the mentioned electrodes is located downstream to the working electrode and the other reference electrode is downstream to the counter electrode. The reference electrode close to the working electrode forms an enclosed circuit with the counter electrode, while the reference close to the counter electrode forms an enclosed circuit to the working electrode. These two enclosed circuits then form another enclosed circuit. When the sample fluid containing measuring analyte is applied to the electrode strip form the front end, it has to be well distributed to cover all the reaction area to be able to trigger an application of excitation potential for the electrochemical reaction. This invention electrode strip checks three points for the wellness of the distribution of the sample fluid: the progress of the sample transferring, the coverage of the counter electrode side and the coverage of the working electrode side. The impedance from the sample fluid has to be able to enclose all three circuits. The circuit is coupled with an operating amplifier which has one input connected to the source of excitation potential.

The invention biosensor can prevent the incorrect result of analysis from insufficient volume or non-homogenous distribution of sample fluids. A fully established circuit requires that the sample fluid be well distributed to cover the working electrode, the counter electrode, and the reference electrodes located down stream of these two mentioned electrodes. Furthermore, a non-homogenous distribution of sample fluid covering the reaction area partially is not able to establish the full circuit. The sample fluid from the counter electrode side has to cover the far end of the working electrode side to be able to establish the circuit and vise versa. With this three-point check, the feathering electrode strip is free of the interference of the poorly diffusing samples such as whole blood or the samples with larger molecules.

Figure 5A:
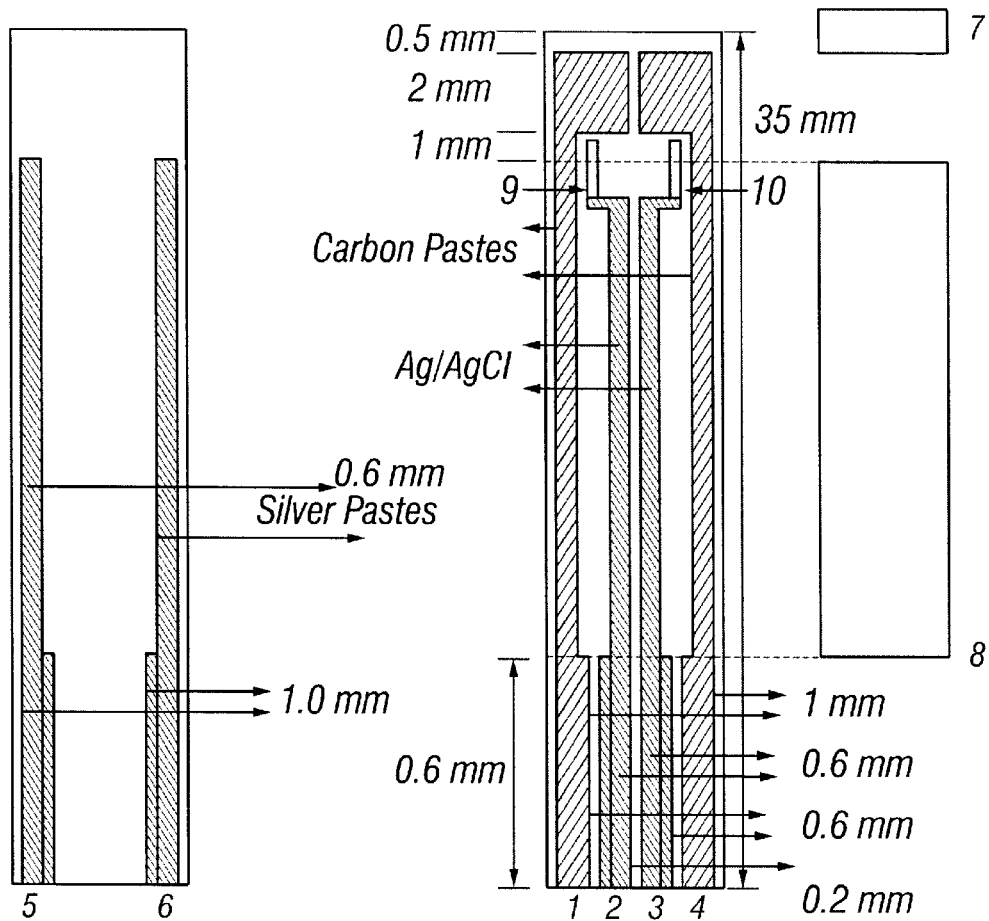
FIG. 5 illustrates an exemplary invention biosensor containing diagonally positioned quadruple electrodes. 5A: top view; and 5B: circuit connections of the quadruple electrodes.
Figure 5B:
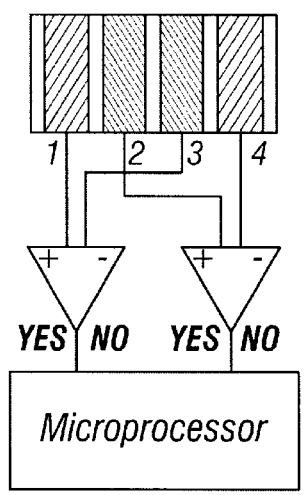

A schematic top view of the preferred screen-printed electrode system of this exemplary invention biosensor is shown in FIG. 5. The working electrode and the counter electrode are made firstly by screen-printing two silver pastes 5 and 6 as lead-conductors and subsequently two conductive carbon pastes 1 and 4 on the insulating substrate. The two reference electrodes 2 and 3 are formed by screen-printing two silver/silver chloride pastes on the insulating substrate. The insulating substrate can be any useful insulating material, such as vinyl polymers, polyesters, and polyimides, capable of providing the electrical and structure properties. The diffusion gap between the working and the counter electrodes is uniformly all around the reaction area. The meter ends of these electrodes are used to make contact with the instrument and the electrode ends of the reference electrodes are arranged that these two front ends 9 and 10 space from each other to the farthest distance without contacting the counter and the working electrodes. They are located downstream of the transferring path of the sample to the working and counter electrodes. The contact bar of the working electrode 1 forms a circuit with the contact bar of the reference electrode 3 which is located downstream to the counter electrode. The contact bar of counter electrode 4 forms another circuit with the contact bar of the reference electrode located downstream to the working electrode. These two circuits are then connected to form another circuit that is connected to a microprocessor. Only when both circuits are closed at the same time that a fill circuit is closed. This circuit is connected with an operational amplifier which has one input connected to the excitation potential. When the impedance after the application of the sample fluid make the switch of the two minor circuits to close, the full circuit is closed shutting down the generation of the excitation potential. After the enzymatic reaction is finished, the excitation potential is generated again and starts the electrochemical reaction. The electronic current generated from the electrochemical reaction is then measured and correlated to the presence or concentration of the analytes.

The reaction area of the electrode strip is formed by covering the electrodes with dielectrical material in the area other than the designed area and the contact bars. The reaction area on the electrodes is defined to be 15 mm$^2$ (=5 mm×3 mm). Within the reaction area, the surface area of the working electrode is 4 mm$^2$ (=2 mm×2 mm), which equals to that of the counter one. Both electrodes in the reaction area are made of the same electrically conducting material (carbon paste in this case). A similar biosensors containing diagonally positioned quadruple electrode is illustrated in FIG. 6.

Although the foregoing descriptions are all related to an amperometric glucose biosensor, this invention is widely applicable to an enzyme-related system such as cholesterol sensor, alcohol sensor, lactate sensor, etc. As mentioned above, the biosensor of the invention is capable of measuring a specific component in various kinds of samples rapidly.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A biosensor for electrochemical analysis of a liquid sample, which biosensor comprises:

a) an insulating base plate having a first end and a second end;

b) an electrode system on said insulating base plate, wherein said electrode system comprises a working electrode and a counter electrode, said working and counter electrodes have conductive leads for connecting said electrodes to a readout device for electrochemical measurement on said first end of said base plate, said working electrode is engulfed by said counter electrode on all sides except the side leading to said conductive leads, and there is a gap space between said working and counter electrodes;

c) a reaction area as part of said electrode system, said reaction area occupies at least a portion of said working electrode, said counter electrode and the gap space between said working electrode and said counter electrode in a direction perpendicular to said conductive leads, said reaction area is defined by covering a non-reaction-area with a layer comprising a dielectrical material, and said reaction area comprises an enzyme that catalyzes a reaction involving an analyte to be analyzed or a substrate that is involved in a reaction catalyzed by an enzyme to be analyzed; and d) a sample application and reaction chamber, wherein the bottom of said chamber is said reaction area defined in c), the top of said chamber is a cover that covers at least said reaction area, said top has an opening above said reaction area for sample application, two side walls of said chamber in a direction perpendicular to said conductive leads are formed by said layer comprising said dielectrical material defined in c), and two sides of said chamber in a direction parallel to said conductive leads are left open as air vents.

2. The biosensor of claim 1, wherein the insulating base plate comprises vinyl polymer(s), polymide(s), polyester(s), nylon, nitrocellulose or a combination thereof.

3. The biosensor of claim 1, wherein the working and counter electrodes are made of substantially identical material(s) within the reaction area.

4. The biosensor of claim 1, wherein the gap space between the working electrode and the counter electrode is kept substantially constant within the reaction area.

5. The biosensor of claim 1, wherein the width of the working electrode is about twice of the width of the counter electrode within the reaction area.

6. The biosensor of claim 1, wherein the surface area of the working electrode is substantially identical to the surface area of the counter electrode within the reaction area.

7. The bio sensor of claim 1, wherein the electrode system is screen-printed printed onto the insulating base plate.

8. The biosensor of claim 7, wherein the working and counter electrodes comprise carbon paste and the conductive leads comprise conductive silver paste.

9. The biosensor of claim 1, wherein the dielectrical material is vinylpolyester(s), polyimide(s) or a combination thereof.

10. The biosensor of claim 1, wherein the thickness of the dielectrical material proximal to the first end is substantially higher than the thickness of the dielectrical material proximal to the second end.

11. The biosensor of claim 10, wherein the thickness of the dielectrical material proximal to the first end is about three times of the thickness of the dielectrical material proximal to the second end.

12. The biosensor of claim 1, wherein the top of the sample application and reaction chamber is the corresponding part of the cover for the entire biosensor.

13. The biosensor of claim 12, wherein the cover for the entire biosensor is a lamina adhered to the non-reaction-area and the opening on the top is a punched hole formed on said lamina.

14. The biosensor of claim 13, wherein the punched hole of the lamina has an arcuate part of the sampling slot protruding into the reaction area to form a convex opening, said convex opening serves as the passage for the sample fluid to the reaction area and the arcuate part of the convex opening provides an auxiliary of propulsion for a quick draw of the sample fluid.

15. The biosensor of claim 1, wherein the insulating base plate is transparent, whereby the liquid sample is introduced on the opposite side of the transparent insulating base plate and the liquid sample movement can be monitored through the transparent insulating base plate.

16. The biosensor of claim 1, further comprising an electron transfer mediator in the reaction area.

17. The biosensor of claim 16, wherein the electron transfer mediator is selected from the group consisting of ferrocene and its derivatives, osmium complex, tetrathiofulvalene, phenazine ethosulfate, benzoquinone and hexacyanoferrate.

18. A method for assaying an analyte or an enzyme in a liquid sample, which method comprises:
 a contacting a liquid sample containing or suspected of containing an analyte or an enzyme with the biosensor of claim 16 under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator comprised in the reaction area of the biosensor, leads to the generation of a current that is capable of being detected by the biosensor; and
 b) detecting the current generated in step a), whereby the presence or amount of the analyte or enzyme in the sample liquid is assessed.

19. A method for assaying an analyte or an enzyme in a liquid sample, which method comprises:
 a) contacting a liquid sample containing or suspected of containing an analyte or an enzyme with the biosensor of claim 1 in the presence of a suitable electron transfer mediator under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator, leads to the generation of a current that is capable of being detected by the biosensor; and
 b) detecting the current generated in step a, whereby the presence or amount of the analyte or enzyme in the sample liquid is assessed.

20. The method of claim 19, wherein the volume of the liquid sample to be contacted with the biosensor is from about 1.5 microliters to about 3.0 microliters.

21. The method of claim 19, wherein the analyte to be detected is glucose.

22. The method of claim 21, wherein the enzyme comprised in the reaction area of the biosensor is glucose oxidase and the electron transfer mediator used in the assay is potassium ferricyanide.

23. A biosensor for electrochemical analysis of a liquid sample, which biosensor comprises:
 a) an insulating base plate having a first end and a second end; and
 b) an electrode system on said insulating base plate, wherein said electrode system comprises a working electrode, a counter electrode, and two reference electrodes, said working, counter and reference electrodes have conductive leads for connecting said electrodes to a readout device for electrochemical measurement on said first end of said base plate, each of said reference electrode is diagonally positioned from said working or counter electrode and there is a gap space between said working/counter, working/reference and reference/reference electrodes, said working electrode and a first reference electrode diagonally positioned from said working electrode forms a first closed circuit and said counter electrode and a second reference electrode diagonally positioned from said counter electrode forms a second closed circuit, said first and second closed circuits are connected to form a third circuit, whereby said third circuit is closed only when both said first and second circuits are closed at the same time.

24. The biosensor of claim 23, wherein the insulating base plate comprises vinyl polymer(s) or polymide(s), polyester (s), nylon, nitrocellulose or a combination thereof.

25. The biosensor of claim 23, wherein the working, counter and reference electrodes are made of substantially identical material(s).

26. The biosensor of claim 23, wherein the gap space between the reference electrodes and the working or counter electrode is kept substantially constant.

27. The biosensor of claim 23, wherein the surface area of the working electrode is substantially identical to the surface area of the counter electrode.

28. The biosensor of claim 23, wherein the electrode system is screen-printed onto the insulating base plate.

29. The biosensor of claim 28, wherein the working, counter and reference electrodes comprise carbon paste and the conductive leads of the electrodes comprise conductive silver paste.

30. The biosensor of claim 23, wherein the reference electrodes are engulfed by the working and counter electrodes on all sides except the side leading to said conductive leads.

31. The biosensor of claim 23, wherein the reference electrodes are separated to the farthest distance without contacting either working or counter electrode.

32. The biosensor of claim 23, wherein at least a portion of the working, counter and reference electrodes and the gap space among the electrodes form a reaction area, said reaction area comprises an enzyme that catalyzes a reaction involving an analyte to be analyzed or a substrate that is involved in a reaction catalyzed by an enzyme to be analyzed.

33. The biosensor of claim 32, further comprising an electron transfer mediator in the reaction area.

34. A method for assaying an analyte or an enzyme in a liquid sample, which method comprises:
   a) contacting a liquid sample containing or suspected of containing an analyte or an enzyme with the biosensor of claim 33 under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator comprised in the reaction area of the biosensor, leads to the generation of a current that is capable of being detected by the biosensor; and
   b) detecting the current generated in step a), whereby the presence or amount of the analyte or enzyme in the sample liquid is assessed.

35. The biosensor of claim 32, wherein the reaction area is a complete cross-section of the electrode system in a direction perpendicular to the conductive leads, the reaction area is defined by covering the non-reaction-area with a layer comprising a dielectrical material, and the biosensor further comprises a sample application and reaction chamber, wherein the bottom of said chamber is the reaction area, the top of said chamber is a cover that covers at least the reaction area, said top has an opening above the reaction area for sample application, the two side walls of said chamber in a direction perpendicular to said conductive leads are formed by the layer comprising the dielectrical material, and the two sides of said chamber in a direction parallel to said conductive leads are left open as air vents.

36. The biosensor of claim 35, wherein the dielectrical material is vinylpolyester(s), polyimide(s) or a combination thereof.

37. The biosensor of claim 35, wherein the thickness of the dielectrical material proximal to the first end is substantially higher than the thickness of the dielectrical material proximal to the second end.

38. The biosensor of claim 37, wherein the thickness of the dielectrical material proximal to the first end is about three times of the thickness of the dielectrical material proximal to the second end.

39. The biosensor of claim 35, wherein the top of the sample application and reaction chamber is the corresponding part of the cover for the entire biosensor.

40. The biosensor of claim 39, wherein the cover for the entire biosensor is a lamina adhered to the non-reaction-area and the opening on the top is a punched hole formed on said lamina.

41. The biosensor of claim 40, wherein the punched hole of the lamina has an arcuate part of the sampling slot protruding into the reaction area to form a convex, said convex serves as the passage for the sample fluid to the reaction area and the arcuate part of the convex provide an auxiliary of propulsion for a quick draw of the sample fluid.

42. The biosensor of claim 35, wherein the insulating base plate is transparent, whereby the liquid sample is introduced on the opposite side of the transparent insulating base plate and the liquid sample movement can be monitored through the transparent insulating base plate.

43. The biosensor of claim 35, further comprising an electron transfer mediator in the reaction area.

44. The biosensor of claim 43, wherein the electron transfer mediator is selected from the group consisting of ferrocene and its derivatives, osmium complex, tetrathioflilvalene, phenazine ethosulfate, benzoquinone and hexacyanoferrate.

45. A method for assaying an analyte or an enzyme in a liquid sample, which method comprises:
   a) contacting a liquid samgle containing or suspected of containing an analyte or an enzyme with the biosensor of claim 35 in the presence of a suitable electron transfer mediator under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator, leads to the generation of a current that is capable of being detected by the biosensor; and
   b) detecting the current generated in step a), whereby the presence or amount of the analyte or enzyme in the sample liquid is assessed.

46. A method for assaying an analyte or an enzyme in a liquid sample, which method comprises:
   a) contacting a liquid sample containing or suspected of containing an analyte or an enzyme with the biosensor of claim 32 in the presence of a suitable electron transfer mediator under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator, leads to the generation of a current that is capable of being detected by the biosensor; and
   b) detecting the current generated in step a), whereby the presence or amount of the analyte or enzyme in the sample liquid is assessed.

47. The method of claim 46, wherein the volume of the liquid sample to be contacted with the biosensor is from about 1.5 microliters to about 3.0 microliters.

48. The method of claim 46, wherein the analyte to be detected is glucose.

49. The method of claim 48, wherein the enzyme comprised in the reaction area of the biosensor is glucose oxidase and the electron transfer mediator used in the assay is potassium ferricyanide.

* * * * *